US008747537B2

United States Patent
Shiga et al.

(10) Patent No.: US 8,747,537 B2
(45) Date of Patent: Jun. 10, 2014

(54) INK CONTAINING HETEROCYCLIC AZO DYE, AND DYE FOR USE IN SAID INK

(71) Applicant: Mitsubishi Chemical Corporation, Chiyoda-ku (JP)

(72) Inventors: Yasushi Shiga, Kanagawa (JP); Utako Takeda, Kanagawa (JP); Shoko Ichinosawa, Kanagawa (JP); Mio Ishida, Kanagawa (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 13/793,851

(22) Filed: Mar. 11, 2013

(65) Prior Publication Data

US 2013/0188238 A1  Jul. 25, 2013

Related U.S. Application Data

(63) Continuation of application No. PCT/JP2011/070526, filed on Sep. 8, 2011.

(30) Foreign Application Priority Data

Sep. 10, 2010  (JP) .................................. 2010-203335
Jan. 7, 2011  (JP) .................................. 2011-002372
Apr. 28, 2011  (JP) .................................. 2011-102267

(51) Int. Cl.
*C09D 11/00* (2014.01)
*C09B 29/033* (2006.01)
*C09B 29/039* (2006.01)
*C09B 29/042* (2006.01)

(52) U.S. Cl.
USPC .................... 106/31.5; 106/31.51; 106/31.44; 534/753; 534/795

(58) Field of Classification Search
USPC ............ 106/31.5, 31.51, 31.44; 534/753, 795; 359/290
See application file for complete search history.

(56) References Cited

U.S. PATENT DOCUMENTS

| | | | |
|---|---|---|---|
| 4,698,651 A | 10/1987 | Moore et al. | |
| 4,764,178 A | 8/1988 | Gregory et al. | |
| 4,829,048 A * | 5/1989 | Gregory et al. | 503/227 |
| 5,126,311 A | 6/1992 | Evans et al. | |
| 5,155,088 A * | 10/1992 | Evans et al. | 503/227 |
| 5,179,207 A | 1/1993 | Krutak et al. | |
| 5,366,951 A * | 11/1994 | Vanmaele | 503/227 |
| 5,510,314 A | 4/1996 | Evans et al. | |
| 5,518,983 A | 5/1996 | Bradbury et al. | |
| 5,635,442 A | 6/1997 | Bradbury et al. | |
| 5,683,956 A | 11/1997 | Bowman et al. | |
| 5,877,301 A * | 3/1999 | Murata et al. | 534/788 |
| 6,200,371 B1 | 3/2001 | Meyrick et al. | |
| 6,235,096 B1 | 5/2001 | Meyrick et al. | |
| 6,302,924 B1 * | 10/2001 | Etzbach et al. | 8/466 |
| 6,344,497 B1 | 2/2002 | Meyrick et al. | |
| 2010/0292450 A1 | 11/2010 | Shiga et al. | |
| 2011/0226998 A1 | 9/2011 | Van De Weijer-Wagemans et al. | |

FOREIGN PATENT DOCUMENTS

| | | |
|---|---|---|
| CN | 101457050 A | 6/2009 |
| JP | 57-141451 | 9/1982 |
| JP | 59-096166 | 6/1984 |
| JP | 60-239291 | 11/1985 |
| JP | 62-55194 | 3/1987 |
| JP | 62-294593 | 12/1987 |
| JP | 2-212566 | 8/1990 |
| JP | 02-212566 | 8/1990 |
| JP | 5-112080 | 5/1993 |
| JP | 5-201150 | 8/1993 |
| JP | 8-505820 | 6/1996 |
| JP | 8-267939 | 10/1996 |
| JP | 09-040659 | 2/1997 |
| JP | 9-109566 | 4/1997 |
| JP | 09-503592 | 4/1997 |
| JP | 2000-313174 | 11/2000 |
| JP | 2004-345270 | 12/2004 |
| JP | 2007-229991 | 9/2007 |
| JP | 2007-531917 | 11/2007 |
| JP | 2009-138189 | 6/2009 |
| WO | 94/08797 | 4/1994 |
| WO | 2005/098524 | 10/2005 |
| WO | 2009/063880 | 5/2009 |
| WO | 2010/031860 | 3/2010 |

OTHER PUBLICATIONS

International Search Report issued on Oct. 18, 2011 in PCT/JP2011/070526 filed Sep. 8, 2011.
Had Raghav Maradiya, et al. "Synthesis, Characterization and Application of Monomeric and Polymeric Dispersed Dyes based on Thiophene Derivatives", 2001, vol. 57, No. 12 pp. 347-354.
Had R. Maradiya, et al. "Studies of Novel Monomeric and Polymeric Azo Disperse Dyes", Journal of Appliced Polymer Science, 2002, vol. 84, pp. 1380-1389.
Robert A. Hayes, et al. "Video-speed electronic paper based on electrowetting", Nature, (Great Britain), 2003, vol. 425, pp. 383-385.
U.S. Appl. No. 14/084,972, filed Nov. 20, 2013, Takeda, et al.
Chinese Office Action issued Dec. 25, 2013, in China Patent Application No. 201180043084.1 (with English translation).

* cited by examiner

*Primary Examiner* — Helene Klemanski
(74) *Attorney, Agent, or Firm* — Oblon, Spivak, McClelland, Maier & Neustadt, L.L.P.

(57) ABSTRACT

The invention relates to an ink which comprises: a low-polarity solvent having a relative permittivity of 3 or less at a measuring frequency of 1 kHz; and a specific heterocyclic azo dye.

18 Claims, No Drawings

INK CONTAINING HETEROCYCLIC AZO DYE, AND DYE FOR USE IN SAID INK

TECHNICAL FIELD

The present invention relates to an ink which contains a low-polarity solvent and a heterocyclic azo dye and to an azo dye suitable for use in the ink. More particularly, the invention relates to an ink which contains a low-polarity solvent and a heterocyclic azo dye having a specific chemical structure and which is useful as a display material, and to a heterocyclic azo dye which has a specific chemical structure and is suitable for use in the ink.

BACKGROUND ART

An electrowetting display is an image display system which includes a substrate and, disposed thereon, a plurality of pixels filled with two phases, i.e., an aqueous medium and an oil-based coloring ink, and in which the affinity of the aqueous medium/oil-based coloring ink interface is controlled for each pixel by means of a voltage application on-off operation to spread/gather the oil-based coloring ink on the substrate and thereby display an image (non-patent document 1). The dyes for use in electrowetting displays are required to have high solubility in low-polarity solvents and high durability, e.g., light fastness (patent document 1 and patent document 2).

Patent document 2 describes a highly light-fast anthraquinone dye for use in electrowetting. In general, anthraquinone dyes have a low molar extinction coefficient and must be used in a higher concentration in order to attain an extinction coefficient substantially the same as that of heterocyclic azo dyes. As a result, higher solubility is required of the anthraquinone dyes. Furthermore, when an anthraquinone dye is used in a high concentration, an increase in viscosity and a change in electrical property occur in the electrowetting. There is hence a possibility that use of the disclosed anthraquinone dye in electrowetting applications might be problematic.

Patent document 3 describes a pyrazole disazo dye having high solubility in hydrocarbon solvents. However, n-decane solutions of the dye are yellow, and the dye does not conform to other color tones.

Patent document 4 and patent document 5 describe red heterocyclic azo dyes which are for use as thermal-transfer dyes and are akin to the dye of the present invention. However, no statement or suggestion concerning solubility in low-polarity solvents is given in the documents.

PRIOR-ART DOCUMENTS

Patent Documents

Patent Document 1: JP-T-2007-531917 (The term "JP-T" as used herein means a published Japanese translation of a PCT patent application.)
Patent Document 2: International Publication WO 2010/031860
Patent Document 3: International Publication WO 2009/063880
Patent Document 4: JP-A-62-294593
Patent Document 5: JP-T-8-505820

Non-Patent Document

Non-Patent Document 1: *Nature*, (Great Britain), 2003, Vol. 425, pp. 383-385

SUMMARY OF THE INVENTION

Problems that the Invention is to Solve

An object of the invention is to provide an ink which contains a heterocyclic azo dye having excellent solubility in low-polarity solvents and having a high extinction coefficient and high light fastness and which is useful as a material for displays and light modulation, and to provide a heterocyclic azo dye suitable for use in the ink.

Means for Solving the Problems

The present inventors diligently made investigations in order to overcome the problems described above. As a result, the inventors have found that a heterocyclic azo dye having a certain chemical structure has excellent solubility in low-polarity solvents, e.g., hydrocarbon solvents, and further has a high molar extinction coefficient and high light fastness. The invention has been accomplished on the basis of these findings.

Essential points of the invention reside in the following (1) to (12).

(1) An ink which comprises: a low-polarity solvent having a relative permittivity, as measured at a frequency of 1 kHz, of 3 or less; and a heterocyclic azo dye, wherein the heterocyclic azo dye is a dye represented by the following general formula (I):

[Chem. 1]

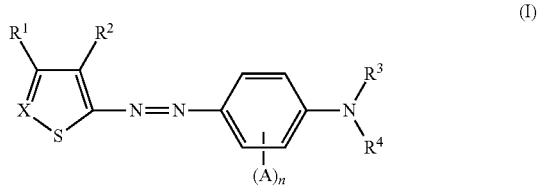

wherein $R^1$ represents a hydrogen atom or an optionally substituted alkyl group having 1-20 carbon atoms, $R^2$ represents a cyano group or a $COOR^5$ group, $R^5$ represents an optionally substituted alkyl group having 1-20 carbon atoms, $R^3$ and $R^4$ each independently represent an optionally substituted alkyl group having 1-20 carbon atoms, A represents a hydrogen atom, a halogen atom, an optionally substituted alkyl group having 1-20 carbon atoms, an optionally substituted alkoxy group having 1-20 carbon atoms, or an $NHCOR^6$ group, n represents an integer of 1-4, and when n is 2 or larger, the A may be the same or different, $R^6$ represents a hydrogen atom, an alkyl group having 1-20 carbon atoms, an alkoxy group having 1-20 carbon atoms, or an aryl group, X represents a nitrogen atom or an optionally substituted methine group, and $R^3$ and $R^4$ may be bonded to each other to form a cyclic structure.

(2) The ink according to (1) above wherein the low-polarity solvent comprises at least one member selected from the group consisting of hydrocarbon solvents, silicone oils, and fluorocarbon solvents.

(3) The ink according to (1) or (2) above wherein the heterocyclic azo dye is a dye in which, when dissolving the dye in n-decane, an absorption-maximum wavelength in the wavelength range of 350-750 nm is in the range of 450-600 nm, and the product of a molar extinction coefficient ε (Lmol$^{-1}$cm$^{-1}$) at the absorption-maximum wavelength and a concentration C (molL$^{-1}$) of saturated solution in the solvent at room temperature (25° C.), εC, has a value of 500 cm$^{-1}$ or larger.

(4) The ink according to any one of (1) to (3) above, which comprises at least one of a pyrazole dye and an alkylamine-substituted anthraquinone dye.

(5) The ink according to (4) above, wherein the pyrazole dye is represented by the following general formula (II) and the alkylamine-substituted anthraquinone dye is represented by the following general formula (III).

[Chem. 2]

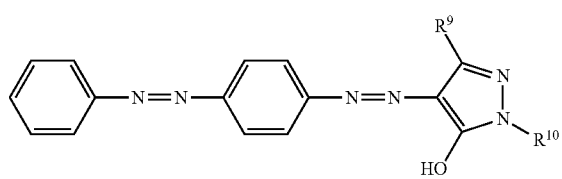

(II)

wherein R$^9$ represents an alkyl group having 2-10 carbon atoms, and R$^{10}$ represents an alkyl group having 3-10 carbon atoms, and the phenyl group and the phenylene group each may independently have a substituent;

[Chem. 3]

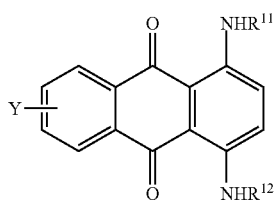

(III)

wherein Y represents a hydrogen atom or a COOR$^{13}$ group, and R$^{11}$ to R$^{13}$ each independently represent an optionally substituted alkyl group having 1-20 carbon atoms, at least one of R$^{11}$ to R$^{13}$ is an optionally substituted branched alkyl group having 4-20 carbon atoms, and the anthraquinone ring may have any substituent other than the Y, NHR$^{11}$ and NHR$^{12}$.

(6) The ink according to any one of (1) to (5) above, which is for use in a display or optical shutter.

(7) A display which comprises a display part that containing the ink according to any one of (1) to (5) above, in which an image is displayed by controlling voltage application to the display part.

(8) The display according to (7) above, wherein the display part contains electrophoretic particles or an aqueous medium.

(9) The display according to (7) or (8) above, wherein an image is displayed by changing the coloration by means of voltage application.

(10) The display according to any one of (7) to (9) above, wherein an image is displayed by an electrowetting system or an electrophoretic system.

(11) An electronic paper which comprises the display according to any one of (7) to (10) above.

(12) A heterocyclic azo dye represented by the following general formula (IV):

[Chem. 4]

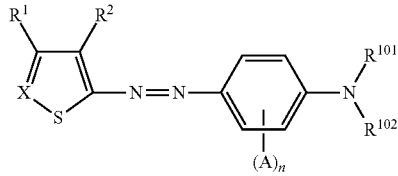

(IV)

wherein

R$^1$ represents a hydrogen atom or an optionally substituted alkyl group having 1-20 carbon atoms, R$^2$ represents a cyano group or a COOR$^5$ group, R$^5$ represents an optionally substituted alkyl group having 1-20 carbon atoms, R$^{101}$ and R$^{102}$ each independently represent an optionally substituted alkyl group having 5-20 carbon atoms, A represents a hydrogen atom, a halogen atom, an optionally substituted alkyl group having 1-20 carbon atoms, an optionally substituted alkoxy group having 1-20 carbon atoms, or an NHCOR$^6$ group, n represents an integer of 1-4, and when n is 2 or larger, the A may be the same or different, R$^6$ represents a hydrogen atom, an alkyl group having 1-20 carbon atoms, an alkoxy group having 1-20 carbon atoms, or an aryl group, X represents a nitrogen atom or an optionally substituted methine group, and R$^{101}$ and R$^{102}$ may be bonded to each other to form a cyclic structure.

Effects of the Invention

The heterocyclic azo dye of the invention has high solubility in oil-soluble solvents and can hence be used extensively as inks. Furthermore, since the heterocyclic azo dye of the invention has high solubility in low-polarity solvents and since the ink which contains the dye has a high molar extinction coefficient and high light fastness, this ink is useful as an ink for use in displays and optical shutters.

MODES FOR CARRYING OUT THE INVENTION

Representative embodiments for carrying out the invention are explained below in detail. However, the invention can be variously modified unless the modifications depart from the spirit of the invention, and should not be construed as being limited to the following embodiments.

The ink of the invention is an ink which includes a low-polarity solvent having a relative permittivity, as measured at a frequency of 1 kHz, of 3 or less and a heterocyclic azo dye, and is characterized in that the heterocyclic azo dye is a dye represented by the following general formula (I):

[Chem. 5]

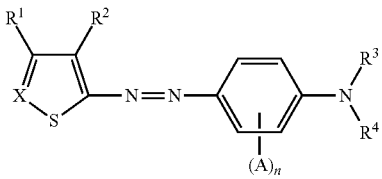

(I)

[wherein
$R^1$ represents a hydrogen atom or an optionally substituted alkyl group having 1-20 carbon atoms,
$R^2$ represents a cyano group or a $COOR^5$ group,
$R^5$ represents an optionally substituted alkyl group having 1-20 carbon atoms,
$R^3$ and $R^4$ each independently represent an optionally substituted alkyl group having 1-20 carbon atoms,
A represents a hydrogen atom, a halogen atom, an optionally substituted alkyl group having 1-20 carbon atoms, an optionally substituted alkoxy group having 1-20 carbon atoms, or an $NHCOR^6$ group,
n represents an integer of 1-4, and when n is 2 or larger, the A atoms or groups may be the same or different,
$R^6$ represents a hydrogen atom, an alkyl group having 1-20 carbon atoms, an alkoxy group having 1-20 carbon atoms, or an aryl group,
X represents a nitrogen atom or an optionally substituted methine group, and
$R^3$ and $R^4$ may have been bonded to each other to form a cyclic structure].

(Low-Polarity Solvent)

In the invention, a low-polarity solvent is used as the solvent of the ink. The ink of the invention can be used, for example, in a display device that has layers such as an aqueous layer and an oily layer and that is based on a phenomenon in which a layer breaks up or a layer moves aside. For clearly displaying images, it is necessary that the ink-containing layer should stably break up or move aside without mingling with the other layer and that the solvent should have low compatibility with the other layer and have low polarity, etc. According to the invention, since the ink contains a specific low-polarity solvent and a heterocyclic azo compound, a layer thereof can stably break up or move aside.

Meanwhile, in display devices based on electrophoresis, in which charged particles (electrophoretic particles) move in a medium by the action of an electric field, there are cases where too high a permittivity of the solution is an obstacle to the operation. Use of the low-polarity solvent and specific heterocyclic azo compound according to the invention makes it possible to color a solution without adversely affecting the movement of the particles.

When the ink of the invention is used in the electrowetting system, there are cases where the contact angle and surface tension of the low-polarity solvent affect the operation of the display device.

The relative permittivity of the low-polarity solvent to be used in the invention, as measured at a frequency of 1 kHz, is 3 or less. The relative permittivity thereof is preferably 2.5 or less, more preferably 2.2 or less. There is no particular lower limit on the relative permittivity thereof. It is, however, preferable that the relative permittivity thereof should be generally 1.5 or higher, preferably 1.7 or higher. A method for measuring the relative permittivity of a low-polarity solvent will be shown in the Examples.

When a layer in which the ink is contained has too high a relative permittivity, there are cases where a trouble arises in the operation of the display device. For example, when the other layer, which contains no ink, is a layer of a liquid having electrical conductivity, polarity, or the like, such as water, a salt solution, or the like, and when the low-polarity solvent used in the ink-containing layer has too high a relative permittivity, then there are cases where the layers mingle with each other.

The viscosity of the low-polarity solvent to be used in the invention is not particularly limited. It is, however, preferred that the viscosity of the solvent having a temperature of 25° C. should be 0.1 $m^2 s^{-1}$ or higher. The viscosity thereof is preferably 10,000 $m^2 s^{-1}$ or less, more preferably 2,000 $m^2 s^{-1}$ or less, especially preferably 1,000 $m^2 s^{-1}$ or less. There are cases where when the viscosity of the solvent is within the adequate range, the dye and other ingredients are easy to dissolve therein and the display device can be operated without arousing a trouble therein. A method for measuring the viscosity of the ink of the invention will be shown in the Examples.

The boiling point of the low-polarity solvent according to the invention is not particularly limited. However, the boiling point thereof is preferably 120° C. or higher, more preferably 150° C. or higher, and is preferably 300° C. or lower. When the solvent has a boiling point which is not too high, this solvent has neither too high a melting point nor too high a viscosity and there are cases where the display device can be operated without arousing a trouble therein. When the boiling point thereof is not too low, the solvent has reduced volatility and there are cases where stability and safety are obtained.

Low-polarity solvents can be used alone or as a mixture thereof. Examples thereof include hydrocarbon solvents, fluorocarbon solvents, silicone oils, and higher fatty acid esters. Examples of the hydrocarbon solvents include linear or branched aliphatic hydrocarbons, alicyclic hydrocarbons, aromatic hydrocarbons, and petroleum naphtha. Examples of the aliphatic hydrocarbon solvents include aliphatic hydrocarbon solvents such as n-decane, isodecane, decalin, nonane, dodecane, isododecane, tetradecane, hexadecane, and isoalkanes, and commercial products thereof include Isopar E, Isopar G, Isopar H, Isopar L, Isopar M (manufactured by Exxon Mobil Corp.), IP Solvent (manufactured by Idemitsu Petrochemical Co., Ltd.), and Soltol (manufactured by Phillips Petroleum International Ltd.). Examples of the aromatic hydrocarbon solvents include Hisosol (manufactured by Nippon Oil Co., Ltd.). Examples of the petroleum naphtha solvents include Shell S.B.R., Shellsol 70, Shellsol 71 (manufactured by Shell Sekiyu K.K.), and Pegasol (manufactured by Exxon Mobil Corp.).

The fluorocarbon solvents are hydrocarbons mainly substituted with fluorine. Examples thereof include perfluoroalkanes represented by $C_nF_{2n+2}$, such as $C_7F_{16}$ and $C_8F_{18}$, and commercial products thereof include Fluorinert PF5080 and Fluorinert PF5070 (manufactured by Sumitomo 3M Ltd.). Examples of fluorochemical inert liquids include Fluorinert FC Series (manufactured by Sumitomo 3M Ltd.). Examples of fluorocarbons include Krytox GPL Series (manufactured by DuPont Japan Ltd.). Examples of chlorofluorocarbons include HCFC-141b (manufactured by Daikin Industries, Ltd.). Examples of iodinated fluorocarbons, such as $F(CF_2)_4 CH_2CH_2I$ and $F(CF_2)_6I$, include I-1420 and I-1600 (manufactured by Daikin Fine Chemical Laboratory Co., Ltd.).

Examples of the silicone oils include low-viscosity synthetic dimethylpolysiloxane, and commercial products thereof include KF96L (manufactured by Shin-Etsu Silicones) and SH200 (manufactured by Dow Corning Toray Silicone Co., Ltd.).

In the invention, it is preferred that the low-polarity solvent should include at least one member selected from hydrocarbon solvents, fluorocarbon solvents, and silicone oils. The content thereof is generally 50% by mass or higher, preferably 70% by mass or higher, more preferably 90% by mass or higher, based on the low-polarity solvent.

The ink of the invention, which includes the low-polarity solvent and a heterocyclic azo dye, is obtained by dissolving the heterocyclic azo dye and optional ingredients, e.g., other dyes and additives, in the low-polarity solvent.

In connection with the term "dissolving", the heterocyclic azo dye need not have been completely dissolved in the low-polarity solvent so long as the solution prepared by dissolving the dye in the low-polarity solvent passes through a filter of about 0.1 μm and is in such a state that the extinction coefficient thereof can be measured. The solution may contain fine particles of the dye dispersed therein.

(Heterocyclic Azo Dye)

The heterocyclic azo dye to be used in the ink of the invention has a chemical structure represented by general formula (I).

In general formula (I), $R^1$ represents a hydrogen atom or an optionally substituted alkyl group having 1-20 carbon atoms. $R^1$ may be bonded to X to form a cyclic structure. From the standpoint of gram extinction coefficient, $R^1$ preferably is a substituent having a low molecular weight, and more preferably is a hydrogen atom or an alkyl group having 1-10 carbon atoms. From the standpoint of production, $R^1$ preferably is an unsubstituted alkyl group, and more preferably is an unsubstituted alkyl group having 1-4 carbon atoms, such as methyl, ethyl, propyl, isopropyl, or butyl.

$R^2$ represents a cyano group or a $COOR^5$ group, and $R^5$ represents an optionally substituted alkyl group having 1-20 carbon atoms. From the standpoint of production or gram extinction coefficient, it is preferred that $R^5$ should be an alkyl group having 1-10 carbon atoms.

$R^3$ and $R^4$ each independently represent an optionally substituted alkyl group having 1-20 carbon atoms. $R^3$ and $R^4$ may be bonded to each other to form a cyclic structure. Furthermore, $R^3$ or $R^4$ may be bonded to $(A)^n$ to form a cyclic structure.

When solubility in low-polarity solvents is taken into account, it is preferred that $R^3$ and/or $R^4$ should be an alkyl group having 2 or more carbon atoms, in particular, an alkyl group having 3 or more carbon atoms, more preferably an alkyl group having 4 or more carbon atoms. Furthermore, it is preferred that $R^3$ and/or $R^4$ should be a branched alkyl group, e.g., isobutyl, isooctyl, or isononyl, and it is especially preferred that $R^3$ and $R^4$ are both a branched alkyl group.

Symbol A in $(A)^n$ represents a hydrogen atom, a halogen atom, an optionally substituted alkyl group having 1-20 carbon atoms, an optionally substituted alkoxy group having 1-20 carbon atoms, or an optionally substituted $NHCOR^6$ group.

Symbol n represents an integer of 1-4, and when n is 2 or larger, the A atoms or groups may be the same or different.

It is preferred that A should be a hydrogen atom, a halogen atom, an alkyl group having 1-4 carbon atoms, such as methyl, ethyl, propyl, isopropyl, cyclopropyl, butyl, isobutyl, sec-butyl, or tert-butyl, an alkoxy group, or an $NHCOR^6$ group such as acetylamino. Especially preferably, A is a hydrogen atom, methyl, or acetylamino.

$R^6$ represents a hydrogen atom, an alkyl group having 1-20 carbon atoms, an alkoxy group having 1-20 carbon atoms, or an aryl group. The aryl group is a group obtained by removing one hydrogen atom from a 5- or 6-membered monocycle or from a fused ring composed of two to four such monocycles fused together. Examples thereof include aromatic hydrocarbon ring groups or aromatic heterocyclic groups, such as phenyl, naphthyl, thienyl, and pyridyl. It is preferred that $R^6$ should be an alkyl group having 1-8 carbon atoms, such as methyl, ethyl, propyl, isopropyl, cyclopropyl, butyl, isobutyl, sec-butyl, tert-butyl, pentyl, isopentyl, neopentyl, tert-pentyl, 2-methylbutyl, 1-methylbutyl, 1,2-dimethylpropyl, 1,1-dimethylpropyl, cyclopentyl, hexyl, 4-methylpentyl, 3-methylpentyl, 2-methylpentyl, 1-methylpentyl, 3,3-dimethylbutyl, 2,3-dimethylbutyl, 1,3-dimethylbutyl, 2,2-dimethylbutyl, 3,3-dimethylbutyl, 1,2-dimethylbutyl, 1,1-dimethylbutyl, 3-ethylbutyl, 2-ethylbutyl, 1-ethylbutyl, 1,2,2-trimethylbutyl, 1,1,2-trimethylbutyl, 1-ethyl-2-methylpropyl, hexyl, cyclohexyl, 2-methylhexyl, 3-methylhexyl, 4-methylhexyl, 5-methylhexyl, 2,4-dimethylpentyl, octyl, 2-ethylhexyl, 2,5-dimethylhexyl, 2,4-dimethylhexyl, 2,5,5-trimethylpentyl, or 2,4,4-trimethylpentyl.

X represents a nitrogen atom or an optionally substituted methine group. In the case where X is a methine group, X may be unsubstituted or may have a substituent. Examples of the substituent which may be possessed by X include optionally substituted alkyl groups having 1-10 carbon atoms, a $COOR^7$ group, and cyano. $R^7$ represents an optionally substituted alkyl group having 1-20 carbon atoms.

It is preferred that X should be a nitrogen atom, a methine group, a methine group substituted with an alkyl group having 1-4 carbon atoms, or a methine group substituted with an alkoxycarbonyl group having 2-5 carbon atoms.

Examples of the alkyl groups represented by $R^1$ and $R^3$ to $R^7$ include: linear alkyl groups such as methyl, ethyl, propyl, butyl, pentyl, hexyl, heptyl, octyl, nonyl, decyl, and dodecyl; branched alkyl groups such as isopropyl, isobutyl, sec-butyl, tert-butyl, isooctyl, and isononyl; and cycloalkyl groups such as cyclopropyl, cyclopentyl, cyclohexyl, and cyclopropylmethyl.

The alkyl groups represented by $R^1$ and $R^3$ to $R^7$ may have any desired substituents. It is preferred that the substituents which may be optionally possessed should be low-polarity substituents, from the standpoint of solubility in low-polarity solvents. Examples of such substituents include: halogen atoms such as fluorine, chlorine, bromine, and iodine atoms; and alkoxy groups having 1-10 carbon atoms, such as methoxy, ethoxy, propoxy, butoxy, isobutoxy, sec-butoxy, and tert-butoxy.

From the standpoint of solubility in low-polarity solvents, it is preferred that the heterocyclic azo dye according to the invention should have one or more branched hydrocarbon chains, e.g., isobutyl or isooctyl.

The number of carbon atoms of each of $R^1$, $R^2$, $R^3$, and $R^4$ in general formula (I) according to the invention is not particularly limited, except for the requirements described above. However, the total number of carbon atoms of $R^1$, $R^2$, $R^3$, and $R^4$ is preferably 10 or more, more preferably 12 or more, and is preferably 30 or less. When the total number of carbon atoms thereof is 10 or more, there are often cases where the dye has improved solubility in solvents. When the total number of carbon atoms thereof is 30 or less, there are cases where it is easy to attain the gram extinction coefficient.

It is preferred from the standpoint of industrial production that the dye according to the invention should satisfy the following and other requirements: the dye has satisfactory crystallinity, is easy to purify, and can be produced through a small number of steps and the starting materials are easily available.

For example, it is preferred that $R^3$ and $R^4$ in general formula (I) should be the same substituent, because there are cases where this dye can be produced through a smaller number of steps. Furthermore, there are cases where the dye which has a high melting point has better crystallinity.

Specific examples of the heterocyclic azo dye represented by general formula (I) are shown in Table 1 and Table 2. However, the invention should not be construed as being limited to the examples unless the invention departs from the spirit thereof.

In Table 1 and Table 2, the $(A)^n$ (n is an integer of 1-4) in general formula (I) is expressed by $A^1$ to $A^4$ (general formula (V)).

[Chem. 6]

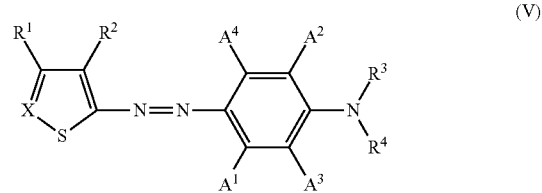

(V)

TABLE 1

| No. | X | $R^1$ | $R^2$ | $R^3$ |
|---|---|---|---|---|
| 1 | N | $CH_2CH_3$ | CN | $i$-$C_4H_9$ |
| 2 | N | $CH_3$ | CN | $CH_2CH(CH_2CH_3)CH_2CH_2CH_2CH_3$ |
| 3 | C—$CO_2CH_2CH_3$ | $CH_3$ | $CO_2CH_2CH_3$ | $CH_2CH(CH_2CH_3)CH_2CH_2CH_2CH_3$ |
| 4 | N | $CH_2CH_3$ | CN | $CH_2CH(CH_2CH_3)CH_2CH_2CH_2CH_3$ |
| 5 | N | $CH_3$ | CN | $CH_2CH(CH_2CH_3)CH_2CH_2CH_2CH_3$ |
| 6 | C—$CO_2CH_2CH_3$ | $CH_3$ | $CO_2CH_2CH_3$ | $CH_2CH(CH_2CH_3)CH_2CH_2CH_2CH_3$ |
| 7 | C—$CO_2CH_2CH_3$ | $CH_3$ | $CO_2CH_2CH_3$ | $CH_2CH(CH_2CH_3)CH_2CH_2CH_2CH_3$ |
| 8 | N | $CH_3$ | CN | $CH_2CH(CH_2CH_3)CH_2CH_2CH_2CH_3$ |
| 9 | N | $CH_3$ | CN | $CH_2CH(CH_2CH_3)CH_2CH_2CH_2CH_3$ |
| 10 | N | $CH_2CH_3$ | CN | $CH_2CH(CH_2CH_3)CH_2CH_2CH_2CH_3$ |
| 11 | N | $CH_2CH_3$ | CN | $CH_2CH(CH_2CH_3)CH_2CH_2CH_2CH_3$ |
| 12 | N | $n$-$C_4H_9$ | CN | $i$-$C_4H_9$ |
| 13 | N | $n$-$C_4H_9$ | CN | $CH_2CH(CH_2CH_3)CH_2CH_2CH_2CH_3$ |
| 14 | N | $i$-$C_3H_7$ | CN | $CH_2CH(CH_2CH_3)CH_2CH_2CH_2CH_3$ |
| 15 | N | $CH_3$ | CN | $CH_2CH(CH_2CH_3)CH_2CH_2CH_2CH_3$ |
| 16 | N | $CH_3$ | CN | $CH_2CH(CH_2CH_3)CH_2CH_2CH_2CH_3$ |
| 17 | N | $CH_3$ | CN | $CH_2CH(CH_2CH_3)CH_2CH_2CH_2CH_3$ |
| 18 | C—$CO_2CH_2CH_3$ | $CH_3$ | $CO_2CH_2CH_3$ | $i$-$C_4H_9$ |
| 19 | C—$CO_2CH_2CH_3$ | $CH_3$ | CN | $CH_2CH(CH_2CH_3)CH_2CH_2CH_2CH_3$ |
| 20 | C—$CO_2CH_2CH_3$ | $CH_3$ | CN | $CH_2CH(CH_2CH_3)CH_2CH_2CH_2CH_3$ |

| No. | $R^4$ | $A^1$ | $A^2$ | $A^3$ | $A^4$ |
|---|---|---|---|---|---|
| 1 | $i$-$C_4H_9$ | $NHCOCH_3$ | H | H | H |
| 2 | $CH_2CH(CH_2CH_3)CH_2CH_2CH_2CH_3$ | $NHCOCH_3$ | H | H | H |
| 3 | $CH_2CH(CH_2CH_3)CH_2CH_2CH_2CH_3$ | $NHCOCH_3$ | H | H | H |
| 4 | $CH_2CH(CH_2CH_3)CH_2CH_2CH_2CH_3$ | $CH_3$ | H | H | H |
| 5 | $n$-$C_8H_{17}$ | $CH_3$ | H | H | H |
| 6 | $CH_2CH(CH_2CH_3)CH_2CH_2CH_2CH_3$ | $CH_3$ | H | H | H |
| 7 | $CH_2CH(CH_2CH_3)CH_2CH_2CH_2CH_3$ | $NHCOCH_2CH_3$ | H | H | H |
| 8 | $CH_2CH(CH_2CH_3)CH_2CH_2CH_2CH_3$ | $CH_2CH_3$ | H | H | H |
| 9 | $CH_2CH(CH_2CH_3)CH_2CH_2CH_2CH_3$ | $NHCOCH_2CH_3$ | H | H | H |
| 10 | $CH_2CH(CH_2CH_3)CH_2CH_2CH_2CH_3$ | $NHCOCH_3$ | H | H | H |
| 11 | $CH_2CH_3$ | $NHCOCH_3$ | H | H | H |
| 12 | $i$-$C_4H_9$ | $NHCOCH_3$ | H | H | H |
| 13 | $CH_2CH(CH_2CH_3)CH_2CH_2CH_2CH_3$ | $CH_3$ | H | H | H |
| 14 | $CH_2CH(CH_2CH_3)CH_2CH_2CH_2CH_3$ | $CH_3$ | H | H | H |
| 15 | $CH_2CH(CH_2CH_3)CH_2CH_2CH_2CH_3$ | $i$-$C_3H_7$ | H | H | H |
| 16 | $CH_2CH(CH_2CH_3)CH_2CH_2CH_2CH_3$ | $CH_3$ | $OCH_3$ | H | H |
| 17 | $CH_2CH(CH_2CH_3)CH_2CH_2CH_2CH_3$ | H | H | H | H |
| 18 | $i$-$C_4H_9$ | $CH_3$ | H | H | H |
| 19 | $CH_2CH(CH_2CH_3)CH_2CH_2CH_2CH_3$ | $CH_3$ | $OCH_3$ | H | H |
| 20 | $CH_2CH(CH_2CH_3)CH_2CH_2CH_2CH_3$ | $CH_2CH_3$ | H | H | H |

TABLE 2

| No. | X | $R^1$ | $R^2$ | $R^3$ |
|---|---|---|---|---|
| 21 | N | $i$-$C_3H_7$ | CN | $i$-$C_4H_9$ |
| 22 | N | $CH_3$ | $CO_2CH_3$ | $CH_2CH(CH_2CH_3)CH_2CH_2CH_2CH_3$ |
| 23 | N | $CH_3$ | $CO_2$-$n$-$C_3H_7$ | $i$-$C_4H_9$ |
| 24 | N | $CH_3$ | CN | $(CF_2)_5CF_3$ |
| 25 | N | $CH_3$ | CN | $CH_2CH(CH_2CH_3)CH_2CH_2CH_2CH_3$ |
| 26 | N | $CH_3$ | CN | $i$-$C_4H_9$ |
| 27 | N | $CH_3$ | CN | $CH_2CH(CH_2CH_3)CH_2CH_2CH_2CH_3$ |
| 28 | C—$CO_2CH_3$ | $CH_3$ | $CO_2CH_3$ | $CH_2CH(CH_2CH_3)CH_2CH_2CH_2CH_3$ |
| 29 | C—$CO_2$-$n$-$C_4H_9$ | $CH_3$ | $CO_2$-$n$-$C_4H_9$ | $i$-$C_4H_9$ |
| 30 | C—$CH_3$ | $CH_3$ | $CO_2CH_3$ | $CH_2CH(CH_2CH_3)CH_2CH_2CH_2CH_3$ |
| 31 | C-$n$-$C_4H_9$ | $CH_3$ | $CO_2CH_3$ | $i$-$C_4H_9$ |
| 32 | C—$CO_2$—$CH_2CH_3$ | $CH_3$ | CN | $CH_2CH(CH_2CH_3)CH_2CH_2CH_2CH_3$ |
| 33 | C—$CO_2$—$CH_2CH_3$ | $CH_3$ | $CO_2$—$CH_2CH_3$ | $CH_2CH(CH_2CH_3)CH_2CH_2CH_2CH_3$ |

TABLE 2-continued

| No. | | | | |
|---|---|---|---|---|
| 34 | C—CO$_2$—CH$_2$CH$_3$ | CH$_3$ | CO$_2$—CH$_2$CH$_3$ | CH$_2$CH(CH$_2$CH$_3$)CH$_2$CH$_2$CH$_2$CH$_3$ |
| 35 | C—CO$_2$—CH$_2$CH$_3$ | CH$_3$ | CN | CH$_2$CH(CH$_2$CH$_3$)CH$_2$CH$_2$CH$_2$CH$_3$ |
| 36 | C—CN | CH$_3$ | CN | CH$_2$CH(CH$_2$CH$_3$)CH$_2$CH$_2$CH$_2$CH$_3$ |
| 37 | C—CN | CH$_3$ | CN | CH$_2$CH(CH$_2$CH$_3$)CH$_2$CH$_2$CH$_2$CH$_3$ |
| 38 | N | CH$_3$ | CN | CH$_2$CH(CH$_2$CH$_3$)CH$_2$CH$_2$CH$_2$CH$_3$ |
| 39 | N | CH$_3$ | CN | CH$_2$CH(CH$_2$CH$_3$)CH$_2$CH$_2$CH$_2$CH$_3$ |
| 40 | C—CO$_2$CH$_3$ | CH$_3$ | CO$_2$CH$_3$ | CH$_2$CH(CH$_2$CH$_3$)CH$_2$CH$_2$CH$_2$CH$_3$ |

| No. | R$^4$ | A$^1$ | A$^2$ | A$^3$ | A$^4$ |
|---|---|---|---|---|---|
| 21 | i-C$_4$H$_9$ | H | H | H | H |
| 22 | CH$_2$CH(CH$_2$CH$_3$)CH$_2$CH$_2$CH$_2$CH$_3$ | NHCOCH$_3$ | H | H | H |
| 23 | i-C$_4$H$_9$ | NHCOCH$_3$ | H | H | H |
| 24 | (CF$_2$)$_5$CF$_3$ | NHCOCH$_3$ | H | H | H |
| 25 | CH$_2$CH(CH$_2$CH$_3$)CH$_2$CH$_2$CH$_2$CH$_3$ | NHCOPh | H | H | H |
| 26 | i-C$_4$H$_9$ | NHCO-i-C$_4$H$_9$ | H | H | H |
| 27 | CH$_2$CH(CH$_2$CH$_3$)CH$_2$CH$_2$CH$_2$CH$_3$ | NHCOCH$_3$ | OCH$_3$ | H | H |
| 28 | CH$_2$CH(CH$_2$CH$_3$)CH$_2$CH$_2$CH$_2$CH$_3$ | Cl | H | CH$_3$ | H |
| 29 | i-C$_4$H$_9$ | NHCOCH$_3$ | CH$_3$ | H | H |
| 30 | CH$_2$CH(CH$_2$CH$_3$)CH$_2$CH$_2$CH$_2$CH$_3$ | CH$_3$ | H | OCH$_3$ | H |
| 31 | i-C$_4$H$_9$ | NHCO-i-C$_4$H$_9$ | H | H | H |
| 32 | CH$_2$CH(CH$_2$CH$_3$)CH$_2$CH$_2$CH$_2$CH$_3$ | NHCOCH$_3$ | H | H | H |
| 33 | CH$_2$CH(CH$_2$CH$_3$)CH$_2$CH$_2$CH$_2$CH$_3$ | NHCOCH$_3$ | OCH$_3$ | H | H |
| 34 | CH$_2$CH(CH$_2$CH$_3$)CH$_2$CH$_2$CH$_2$CH$_3$ | CH$_3$ | OCH$_3$ | H | H |
| 35 | CH$_2$CH(CH$_2$CH$_3$)CH$_2$CH$_2$CH$_2$CH$_3$ | CH$_3$ | H | H | H |
| 36 | CH$_2$CH(CH$_2$CH$_3$)CH$_2$CH$_2$CH$_2$CH$_3$ | NHCOCH$_3$ | H | H | H |
| 37 | CH$_2$CH(CH$_2$CH$_3$)CH$_2$CH$_2$CH$_2$CH$_3$ | CH$_3$ | H | H | H |
| 38 | CH$_2$CH(CH$_2$CH$_3$)CH$_2$CH$_2$CH$_2$CH$_3$ | NHCOCH$_3$ | Cl | H | H |
| 39 | CH$_2$CH(CH$_2$CH$_3$)CH$_2$CH$_2$CH$_2$CH$_3$ | F | H | H | H |
| 40 | CH$_2$CH(CH$_2$CH$_3$)CH$_2$CH$_2$CH$_2$CH$_3$ | Cl | CH$_3$ | H | H |

Preferred of the heterocyclic azo dyes according to the invention is a dye represented by general formula (IV).

[Chem. 7]

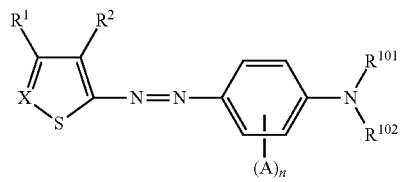

(IV)

[In general formula (IV), $R^1$ represents a hydrogen atom or an optionally substituted alkyl group having 1-20 carbon atoms, $R^2$ represents a cyano group or a COOR$^5$ group, $R^5$ represents an optionally substituted alkyl group having 1-20 carbon atoms, $R^{101}$ and $R^{102}$ each independently represent an optionally substituted alkyl group having 5-20 carbon atoms, A represents a hydrogen atom, a halogen atom, an optionally substituted alkyl group having 1-20 carbon atoms, an optionally substituted alkoxy group having 1-20 carbon atoms, or an NHCOR$^6$ group, n represents an integer of 1-4, and when n is 2 or larger, the A atoms or groups may be the same or different, $R^6$ represents a hydrogen atom, an alkyl group having 1-20 carbon atoms, an alkoxy group having 1-20 carbon atoms, or an aryl group, X represents a nitrogen atom or an optionally substituted methine group, and $R^{101}$ and $R^{102}$ may have been bonded to each other to form a cyclic structure.]

The substituents other than $R^{101}$ and $R^{102}$, in general formula (IV), are the same as in general formula (I). $R^{101}$ and $R^{102}$ in general formula (IV) each independently represent an optionally substituted alkyl group having 5-20 carbon atoms. The number of carbon atoms of each of the alkyl groups represented by $R^{101}$ and $R^{102}$ is preferably 5 or more, more preferably 6 or more, and is preferably 20 or less.

When the number of carbon atoms thereof is 5 or more, there are cases where this dye has better solubility in low-polarity solvents. When the number of carbon atoms thereof is 20 or less, there are cases where a suitable gram extinction coefficient is easy to attain.

It is preferred that $R^{101}$ and $R^{102}$ should be branched, and it is more preferred that both should be branched. $R^{101}$ and $R^{102}$ may be bonded to each other to form a cyclic structure, and $R^{101}$ and $R^{102}$ each may be bonded to (A)$_n$ to form a cyclic structure.

There are cases where the dye in which one of $R^{101}$ and $R^{102}$ in general formula (IV) is an alkyl group having 5 or less carbon atoms but the other has 5 or more carbon atoms and in which $R^1$ has 2 or more carbon atoms and the dye in which $R^{101}$ and $R^{102}$ each have 5 or less carbon atoms but $R^1$ has 4 or more carbon atoms have satisfactory solubility in low-polarity solvents or have a large value of εC.

Furthermore, even when either $R^{101}$ or $R^{102}$ is an alkyl group having 5 or less carbon atoms or both $R^{101}$ and $R^{102}$ are alkyl groups having 5 or less carbon atoms, there are cases where this dye has satisfactory solubility in low-polarity solvents or has a large value of εC when the number of carbon atoms of $R^2$ or the number of carbon atoms of (A)$_n$ is large.

The total number of carbon atoms of $R^1$, $R^2$, $R^{101}$, and $R^{102}$ in general formula (IV) according to the invention is preferably 10 or more, more preferably 12 or more, and is preferably 30 or less. When the total number of carbon atoms thereof is 10 or more, there are often cases where this dye has improved solubility in solvents. When the total number of carbon atoms thereof is 30 or less, there are cases where a suitable gram extinction coefficient is easy to attain.

From the standpoint of gram extinction coefficient, the molecular weight of the heterocyclic azo dye according to the invention is generally 3,000 or less, preferably 1,500 or less, and are generally 300 or higher, in terms of the molecular weight including that of, if any, substituents.

Dyes represented by general formulae (I) and (IV) can be synthesized, for example, by the methods described in the Examples. However, the dyes can be suitably synthesized by known methods.

The heterocyclic azo dye according to the invention is characterized by having excellent solubility in low-polarity solvents, in particular, in hydrocarbon solvents. The heterocyclic azo dye according to the invention has a solubility in room-temperature (25° C.) n-decane of generally 1% by mass or higher, preferably 3% by mass or higher, more preferably 5% by mass or higher. The higher the solubility, the more the dye is preferred. However, the solubility thereof is generally up to about 80% by mass.

In the case where the heterocyclic azo dye according to the invention is to be used in electrowetting displays, it is desirable that the dye should be water-insoluble, in view of the principle thereof. The term "water-insoluble" herein means that the solubility in water, as measured under the conditions of 25° C. and 1 atm, is 0.1% by mass or less, preferably 0.01% by mass or less.

The heterocyclic azo dye according to the invention has a red tone. It is preferred that when the dye is dissolved in a low-polarity solvent and the solution is examined in the wavelength range of 350-750 nm, this solution should have an absorption-maximum wavelength in the range of 450-600 nm. It is preferred that when the dye is dissolved in each of n-decane, tetradecane, Isopar G, Isopar M, and decalin as a solvent and each solution is examined in the wavelength range of 350-750 nm, this solution should have an absorption-maximum wavelength in the range of 450-600 nm. It is also preferred that each solution should have a molar extinction coefficient of 40,000 (Lmol$^{-1}$cm$^{-1}$) or higher.

Furthermore, when the heterocyclic azo dye according to the invention is dissolved in each of n-decane, tetradecane, Isopar G, Isopar M, and decalin as a solvent, the product of the molar extinction coefficient $\epsilon$ (Lmol$^{-1}$cm$^{-1}$) at the absorption-maximum wavelength and the concentration C (molL$^{-1}$) of the saturated solution in each solvent at room temperature (25° C.), $\epsilon$C, has a value which is generally 500 cm$^{-1}$ or larger, preferably 1,000 cm$^{-1}$ or larger, more preferably 2,000 cm$^{-1}$ or larger. The larger the value of $\epsilon$C, the more the dye is preferred. Although there is no particular upper limit thereon, the value of $\epsilon$C is generally 40,000 cm$^{-1}$ or less.

With respect to the concentration of the heterocyclic azo dye in the ink of the invention, the ink is prepared so as to have any desired concentration in accordance with the intended use thereof. For example, in the case where the dye is to be used as a red dye for electrowetting displays, the dye is used after being diluted with a solvent to a concentration of generally 1% by mass or higher in accordance with the desired value of $\epsilon$C. However, the concentration thereof is preferably 1% by mass or higher, more preferably 1.5% by mass or higher. Although higher concentrations are preferred, the concentration of the dye is usually about 80% by mass or less.

The ink of the invention contains at least one dye which is the heterocyclic azo dye described above, and any desired two or more dyes which each are the heterocyclic azo dye may be contained in combination in the ink in any desired proportion.

The heterocyclic azo dye according to the invention has excellent solubility in low-polarity solvents and has a high extinction coefficient and high light fastness. This dye is hence useful as a display material, in particular, an electrowetting display material.

There is no particular lower limit on the viscosity of the ink of the invention which has a temperature of 25° C. However, it is usually preferred that the viscosity thereof should be 0.1 m$^2$s$^{-1}$ or higher. Meanwhile, the upper limit thereof is preferably 10,000 m$^2$s$^{-1}$ or less, more preferably 2,000 m$^2$s$^{-1}$ or less, especially preferably 1,000 m$^2$s$^{-1}$ or less. When the ink has too high a viscosity, there are cases where this ink arouses a trouble in the operation of the display device. A method for measuring the viscosity of the ink of the invention will be shown in the Examples.

With respect to the relative permittivity and viscosity of the solvent according to the invention and those of the ink, which contains the solvent and other ingredients including the dye, it is preferred that the difference between the solvent and the ink in relative permittivity or viscosity should be smaller, because influences on the operation characteristics in the case of use in display devices or the like are lessened in this case. Consequently, although any desired additives suitable for each application may be contained in the ink of the invention according to need so long as this inclusion does not lessen the effects of the invention, it is preferred that the properties of the solvent should be kept unchanged.

(Other Dyes)

The ink of the invention may be made to contain other dyes besides the heterocyclic azo dye in order to obtain a desired color tone. For example, it is possible to mix a yellow dye and a blue dye with the heterocyclic azo dye according to the invention to render the ink black.

Other dyes which may be contained in the ink of the invention can be selected at will from dyes which are soluble or dispersible in the solvent to be used in the invention, so long as the selected dyes do not lessen the effects of the invention.

In the case where the ink of the invention is to be used in electrowetting displays, any desired dyes can be selected from dyes soluble in low-polarity solvents, e.g., aliphatic hydrocarbon solvents, and used as other dyes. Specific examples thereof include: Oil Blue N (alkylamine-substituted anthraquinone), Solvent Green, Solvent Blue, Sudan Blue, Sudan Red, Sudan Yellow, and Sudan Black; the dyes shown in International Publication WO 2009/063880; and the dyes shown in International Publication WO 2010/031860. These dyes themselves are known and are available as commercial products.

Preferred other dyes which may be contained in the ink of the invention are pyrazole disazo dyes, alkylamine-substituted anthraquinone dyes, and heterocyclic azo dyes other than those specified in the invention. A preferred black ink can be rendered possible by using these dyes in any desired combination. It is especially preferred that the ink should contain a pyrazole dye and/or an alkylamine-substituted anthraquinone dye as other dye(s).

Examples of the pyrazole disazo dyes are not particularly limited. However, dyes represented by the following general formula (II) are preferred.

[Chem. 8]

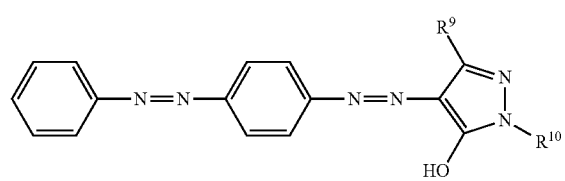

(II)

[In general formula (II), R$^9$ represents an alkyl group having 2-10 carbon atoms, and R$^{10}$ represents an alkyl group having 3-10 carbon atoms. The phenyl group and the phenylene group each may independently have a substituent.]

Examples of the alkyl group having 2-10 carbon atoms which is represented by $R^9$ include: linear alkyl groups having 2-10 carbon atoms, such as ethyl, propyl, butyl, pentyl, hexyl, heptyl, octyl, nonyl, and decyl; branched alkyl groups having 3-10 carbon atoms, such as isopropyl, isobutyl, sec-butyl, tert-butyl, 2-ethylhexyl, and isononyl; and cycloalkyl groups having 3-10 carbon atoms, such as cyclopropyl, cyclobutyl, cyclopentyl, cyclohexyl, cyclopropylmethyl, cyclohexylmethyl, and 4-butylmethylcyclohexyl.

It is especially preferred that $R^9$ should be a linear alkyl group having 2-5 carbon atoms, such as ethyl, propyl, butyl, pentyl, or hexyl.

$R^{10}$ has the same meaning as the alkyl groups having 3-10 carbon atoms among the alkyl groups having 2-10 carbon atoms which were shown above as examples of $R^9$. From the standpoints of high gram extinction coefficient and the easy availability of starting materials, it is preferred that $R^{10}$ should be an alkyl group having 3-6 carbon atoms. From the standpoint of solubility in nonpolar solvents, branched alkyl groups are preferred, and it is most preferred that $R^{10}$ should be tert-butyl.

$R^9$ and $R^{10}$ may have any desired substituents. It is preferred that the substituents which may be optionally possessed should be substituents which do not adversely affect solubility in low-polarity solvents. Examples thereof include halogen atoms such as fluorine, chlorine, bromine, and iodine atoms.

In general formula (II), the phenyl group and the phenylene group each may independently have a substituent.

From the standpoint of solubility in low-polarity solvents, e.g., hydrocarbon solvents, it is preferred that the substituent which may be possessed by the phenyl group should be a nonpolar substituent. Examples thereof include alkyl groups having 1-10 carbon atoms, alkoxy groups having 1-10 carbon atoms, haloalkyl groups having 1-10 carbon atoms, and haloalkoxy groups having 1-10 carbon atoms. Preferred of these are alkyl groups having 1-10 carbon atoms and/or alkoxy groups having 1-10 carbon atoms.

Examples of the alkyl groups having 1-10 carbon atoms include: linear alkyl groups such as propyl, butyl, pentyl, hexyl, heptyl, octyl, nonyl, and decyl; branched alkyl groups such as isopropyl, isobutyl, sec-butyl, tert-butyl, and isooctyl; and alkyl groups having a cycloalkane structure, such as cyclopropyl, cyclopentyl, cyclohexyl, and cyclopropylmethyl.

Examples of the alkoxy groups having 1-10 carbon atoms include: linear alkoxy groups such as methoxy, ethoxy, propoxy, butoxy, pentyloxy, hexyloxy, heptyloxy, octyloxy, nonyloxy, and decyloxy; branched alkoxy groups such as isopropoxy, isobutoxy, sec-butoxy, tert-butoxy, and isooctyloxy; and alkoxy groups having a cycloalkane structure, such as cyclopropoxy, cyclopentyloxy, cyclohexyloxy, and cyclopropylmethyloxy.

The haloalkyl groups and the haloalkoxy groups are groups formed by substituting the alkyl groups and the alkoxy groups with one or more halogen atoms, e.g., fluorine, chlorine, bromine, or iodine atoms. Specific examples thereof include trifluoromethyl, pentafluoroethyl, nonafluorobutyl, and trifluoromethoxy.

Examples of the substituent which may be possessed by the phenylene group include the same groups as those enumerated above as examples of the substituent of the phenyl group. Preferred of these are alkyl groups having 1-10 carbon atoms and/or alkoxy groups having 1-10 carbon atoms. Especially preferred examples of the substituent include alkyl groups having 1-4 carbon atoms, such as methyl and ethyl, and alkoxy groups having 1-4 carbon atoms, such as methoxy and ethoxy.

Specific examples of the dyes represented by general formula (II) are shown below. However, the invention should not be construed as being limited to the following examples unless the invention departs from the spirit thereof. Especially preferred compounds among the dyes represented by general formula (II) include the following compounds.

[Chem. 9]

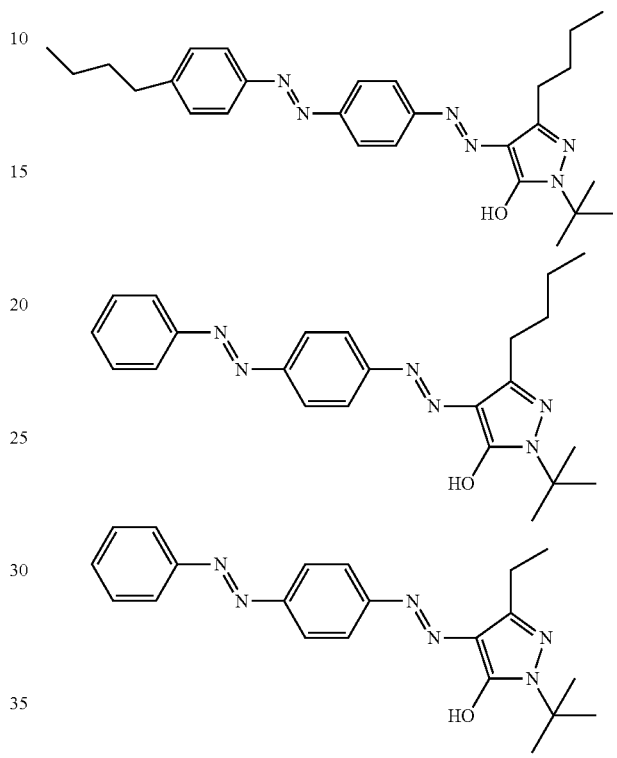

The dyes represented by general formula (II) can be synthesized, for example, by the method described in International Publication WO 2009/063880.

From the standpoint of gram extinction coefficient, the molecular weights of the pyrazole disazo dyes are generally 2,000 or less, preferably 1,000 or less, in terms of the molecular weight including that of, if any, substituents.

The alkylamine-substituted anthraquinone dyes are not particularly limited. However, dyes represented by the following general formula (III) are preferred.

[Chem. 10]

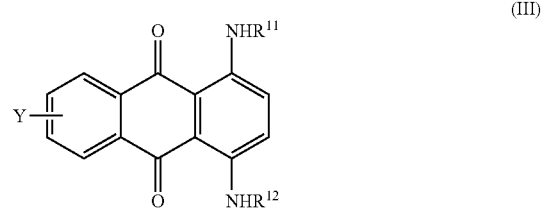

[In general formula (III), Y represents a hydrogen atom or a $COOR^{13}$ group, and $R^{11}$ to $R^{13}$ each independently represent an optionally substituted alkyl group having 1-20 carbon atoms, at least one of $R^{11}$ to $R^{13}$ being an optionally substituted branched alkyl group having 4-20 carbon atoms. The anthraquinone ring may have any substituent besides the Y, $NHR^{11}$, and $NHR^{12}$.]

Examples of the alkyl groups having 1-20 carbon atoms which are represented by $R^{11}$ to $R^{13}$ include: linear alkyl groups having 1-20 carbon atoms, preferably 1-10 carbon atoms, such as methyl, ethyl, propyl, butyl, pentyl, hexyl, heptyl, octyl, nonyl, and decyl; branched alkyl groups having 3-20 carbon atoms, preferably 3-10 carbon atoms, such as isopropyl, isobutyl, sec-butyl, tert-butyl, and isooctyl; and cycloalkyl groups having 3-20 carbon atoms, preferably 3-10 carbon atoms, such as cyclopropyl, cyclobutyl, cyclopentyl, cyclohexyl, cyclopropylmethyl, cyclohexylmethyl, and 4-butylmethylcyclohexyl.

At least one of $R^{11}$ to $R^{13}$ is an optionally substituted branched alkyl group having 4-20 carbon atoms. Examples thereof include isobutyl, sec-butyl, tert-butyl, and isooctyl. Preferred examples thereof include branched alkyl groups having 4-10 carbon atoms, such as sec-butyl, tert-butyl, and isooctyl.

The alkyl groups having 1-20 carbon atoms and branched alkyl groups having 4-20 carbon atoms which are represented by $R^{11}$ to $R^{13}$ may further have substituents. From the standpoint of solubility in low-polarity solvents, those substituents preferably are low-polarity substituents. More specifically, examples thereof include: halogen atoms such as fluorine, chlorine, bromine, and iodine atoms; and alkoxy groups having 1-10 carbon atoms, such as methoxy, ethoxy, propoxy, butoxy, isobutoxy, sec-butoxy, and tert-butoxy.

Furthermore, the anthraquinone ring in general formula (III) may have any desired substituent besides the Y, $NHR^{11}$, and $NHR^{12}$. Examples of the substituent include: halogen atoms such as fluorine, chlorine, bromine, and iodine atoms; and alkyl groups having 1-10 carbon atoms, such as methyl, ethyl, propyl, isopropyl, butyl, isobutyl, sec-butyl, and tert-butyl.

Preferred examples of the dyes represented by general formula (III) are shown below. However, the invention should not be construed as being limited to the following examples unless the invention departs from the spirit thereof.

[Chem. 11]

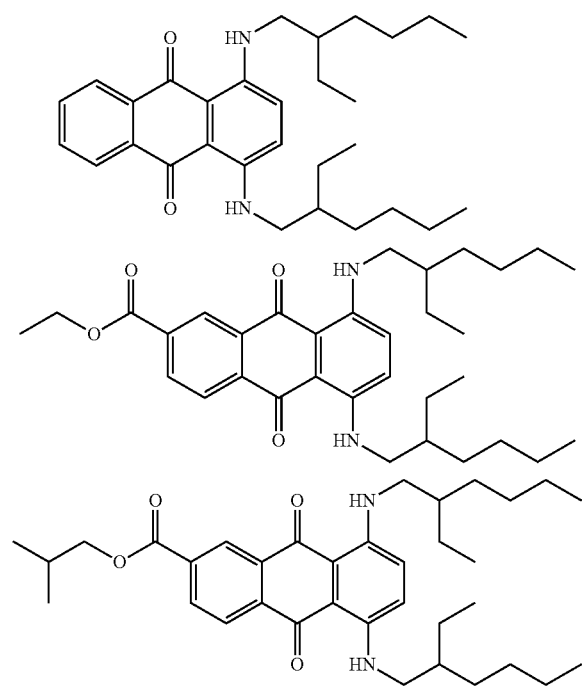

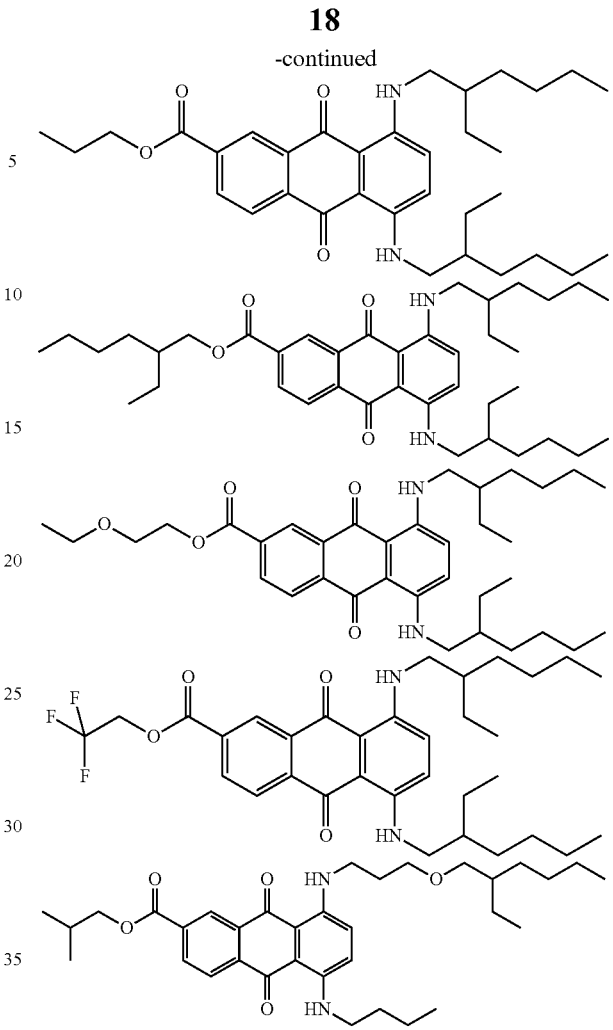

The dyes represented by general formula (III) can be synthesized, for example, by the method described in JP-A-2000-313174.

From the standpoint of gram extinction coefficient, the molecular weights of the alkylamine-substituted anthraquinone dyes according to the invention described above are generally 2,000 or less, preferably 1,000 or less, and are generally 300 or higher, preferably 400 or higher, in terms of the molecular weight including that of, if any, substituents.

With respect to the concentration of the dyes of general formulae (II) and (III) in the ink, the ink is prepared so as to have any desired concentration in accordance with the intended use thereof. In the case where the dyes are to be used as dyes for electrowetting displays, the dyes are used after being diluted with a low-polarity solvent to a concentration of generally 0.2% by mass or higher in accordance with the desired value of εC. However, the concentration thereof is preferably 1% by mass or higher, more preferably 5% by mass or higher. Although higher concentrations are preferred, the concentration of the dyes is usually about 40% by mass or less.

In the invention, it is preferred that dyes represented by general formulae (I), (II), and (III) should be contained in order to obtain a preferred black ink. Inclusion of these dyes makes it possible to attain high light absorption in a wide wavelength range within the visible light region. Use of these dyes is superior in that even when these dyes are used as a mixture thereof, the solubility thereof in solvents does not decrease and the dyes show high solubility. Furthermore, even when those dyes are used as a mixture thereof, the light fastness thereof does not deteriorate and the dyes show high light fastness. Use of these dyes is superior in this respect.

Furthermore, the ink of the invention may contain any desired additives suitable for each application, according to need so long as the additives do not lessen the effects of the invention.

(Applications)

The ink of the invention is suitable for use in displays. With respect to the displays, the ink is especially useful in a display which has a display part that contains an ink and in which an image is displayed by controlling voltage application to the display part, a display in which an image is displayed by changing the coloration by means of voltage application, and a display in which the display part is made to display an image using electrophoretic particles or an aqueous medium.

The electrophoretic particles are charged particles and may have a color. Multiple kinds of electrophoretic particles may be contained in the display part. Meanwhile, the aqueous medium is a fluid which may have a color, and the display part may have multiple kinds of aqueous media. Examples of the aqueous medium include water, non-charged liquids, liquids having an affinity for water, and liquids which are akin to water in surface tension. Examples thereof include alcohols, such as diols and triols, and liquids which contain an inorganic salt, e.g., an alkali metal halide.

Furthermore, the heterocyclic azo dye and ink of the invention are especially useful as inks for use in electrowetting type displays or electrophoresis type displays.

It is also possible to provide a satisfactory black ink having an excellent black hue by using the heterocyclic azo dye of the invention in combination with other dye(s). The dye of the invention is useful also as a member which functions as an optical shutter.

Although usable in any display device which has a display, the ink of the invention is especially useful in electronic paper.

Examples of display technologies include the electrowetting system and the electrophoretic system. Examples of applications of such displays include various displays for computers, for electronic paper, and for electronic inks. There is a possibility that such displays might be capable of replacing most of the current liquid-crystal display applications. It is especially preferred to use the ink of the invention as an ink for electrowetting displays.

EXAMPLES

The invention will be explained below in more detail by reference to Examples and Comparative Examples, but the invention should not be construed as being limited to the following Examples.

<Synthesis of Intermediate C-1>

[Chem. 12]

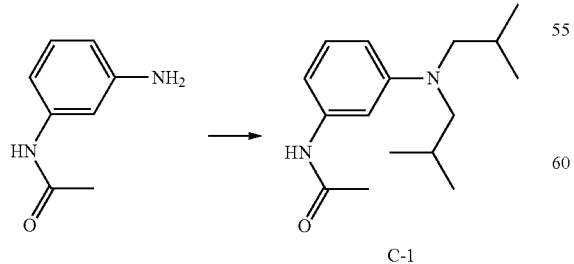

C-1

A mixture of m-aminoacetanilide (8.4 g, 56 mmol), N-methyl-2-pyrrolidone (70 mL), isobutyl iodide (25.7 g, 139 mmol), and potassium carbonate (23.0 g, 166 mmol) was stirred at 140° C. for 13 hours. After this mixture was allowed to cool, desalted water was added thereto. The crystals yielded were taken out by filtration and recrystallized from methanol to obtain C-1 (5.2 g; yield, 35%).

<Synthesis of Intermediate C-2>

[Chem. 13]

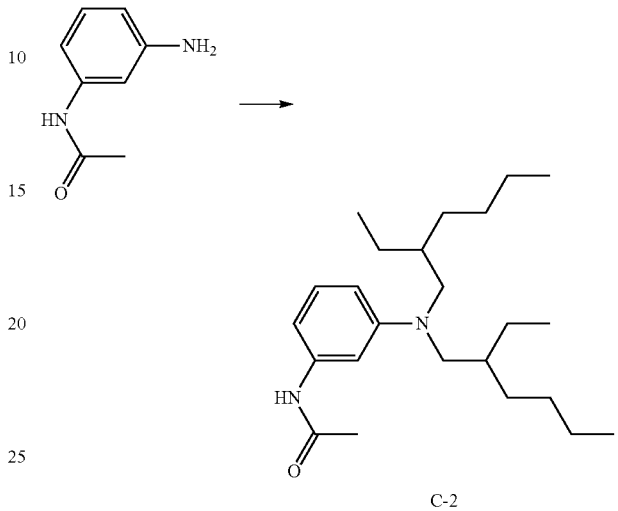

C-2

A mixture of m-aminoacetanilide (13.0 g, 87 mmol), N,N-dimethylformamide (60 mL), 1-bromo-2-ethylhexane (50.4 g, 261 mmol), and potassium carbonate (49.5 g, 358 mmol) was stirred at 140° C. for 14 hours. This mixture was allowed to cool and then filtered. Water was added to the filtrate, and the resultant mixture was extracted with toluene. The organic layer obtained was concentrated and then purified by silica gel column chromatography to obtain C-2 (17.4 g; yield 54%).

<Synthesis of Intermediates C-3 and C-4>

[Chem. 14]

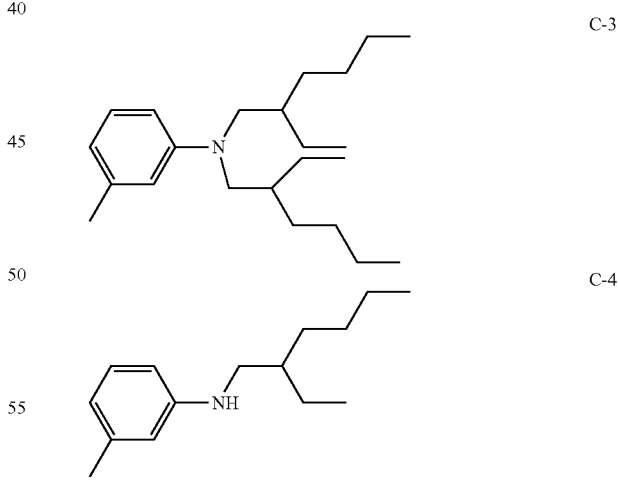

A mixture of m-aminotoluidine (10.0 g, 93 mmol), N,N-dimethylformamide (50 mL), 1-bromo-2-ethylhexane (54.1 g, 280 mmol), and potassium carbonate (51.6 g, 373 mmol) was stirred at 110° C. for 15 hours. This mixture was allowed to cool and then filtered. Water was added to the filtrate, and the resultant mixture was extracted with toluene. The organic layer obtained was concentrated and then purified by silica gel column chromatography to obtain C-3 (24.8 g; yield 80%) and C-4 (5.0 g; yield, 20%).

<Synthesis of Intermediate C-5>

[Chem. 15]

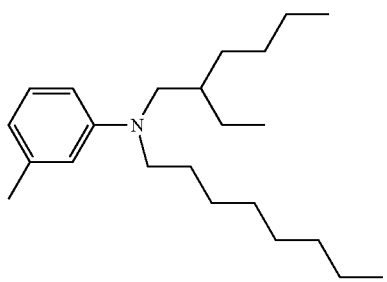

C-5

A mixture of C-4 (5.0 g, 23 mmol), N,N-dimethylformamide (28 mL), 1-bromooctane (6.6 g, 34 mmol), and potassium carbonate (6.3 g, 46 mmol) was stirred at 120° C. for 12 hours. This mixture was allowed to cool and then filtered. Water was added to the filtrate, and the resultant mixture was extracted with toluene. The organic layer obtained was concentrated and then purified by silica gel column chromatography to obtain C-5 (2.2 g; yield 29.1%).

<Synthesis of Intermediate C-6>

[Chem. 16]

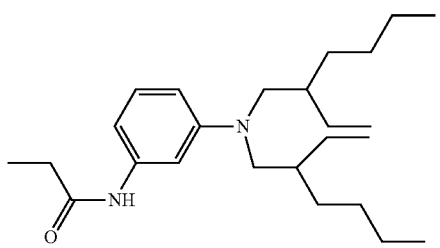

C-6

A mixture of N-(3-aminophenyl)propanamide (10.0 g, 61 mmol), N,N-dimethylformamide (50 mL), 1-bromo-2-ethylhexane (35.3 g, 183 mmol), and potassium carbonate (33.7 g, 244 mmol) was stirred at 110° C. for 24 hours. This mixture was allowed to cool and then filtered. Water was added to the filtrate, and the resultant mixture was extracted with toluene. The organic layer obtained was concentrated and then purified by silica gel column chromatography to obtain C-6 (7.6 g; yield 32%).

<Synthesis of Intermediate C-7>

[Chem. 17]

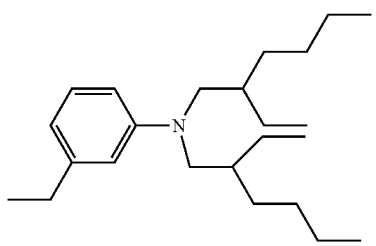

C-7

A mixture of 3-ethylaniline (10.0 g, 83 mmol), N,N-dimethylformamide (50 mL), 1-bromo-2-ethylhexane (47.8 g, 248 mmol), and potassium carbonate (45.6 g, 330 mmol) was stirred at 110° C. for 24 hours. This mixture was allowed to cool and then filtered. Water was added to the filtrate, and the resultant mixture was extracted with toluene. The organic layer obtained was concentrated and then purified by silica gel column chromatography to obtain C-7 (6.3 g; yield 22%).

<Synthesis of Intermediate C-8>

[Chem. 18]

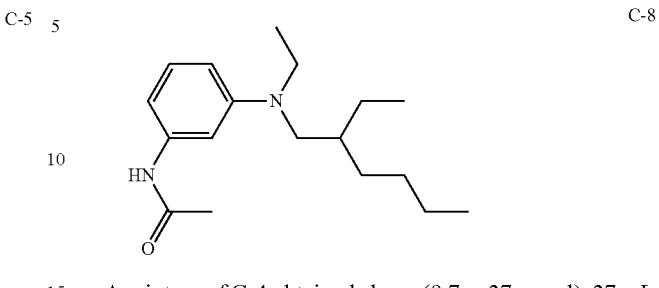

C-8

A mixture of C-4 obtained above (9.7 g, 37 mmol), 37 mL of N-methylpyrrolidone, 11.8 g (76 mmol) of iodoethane, and 8.0 g (75 mmol) of sodium carbonate was stirred at 70° C. for 3.5 hours. This mixture was allowed to cool and then filtered. Water was added to the filtrate, and the resultant mixture was extracted with toluene. The organic layer obtained was concentrated and then purified by silica gel column chromatography to obtain C-8 (8.6 g; yield 80%).

<Synthesis of Intermediate C-9>

[Chem. 19]

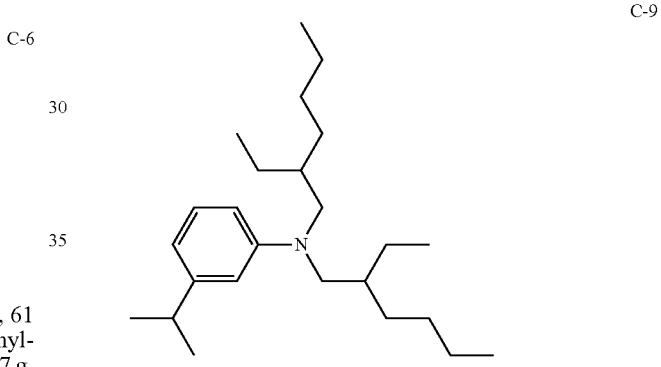

C-9

A mixture of 3-isopropylaniline (10.0 g, 74 mmol), N,N-dimethylformamide (50 mL), 1-bromo-2-ethylhexane (42.8 g, 220 mmol), and potassium carbonate (40.9 g, 300 mmol) was stirred at 140° C. for 20 hours. This mixture was allowed to cool and then filtered. Water was added to the filtrate, and the resultant mixture was extracted with toluene. The organic layer obtained was concentrated and then purified by silica gel column chromatography to obtain C-9 (8.56 g; yield 32%).

<Synthesis of Intermediate C-10>

[Chem. 20]

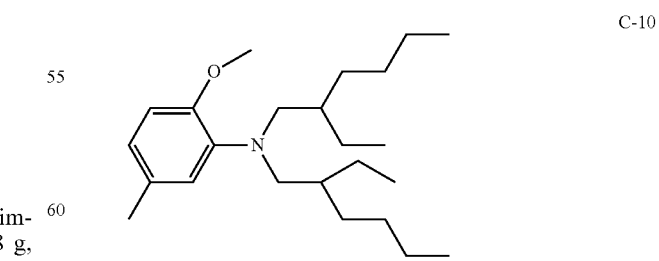

C-10

A mixture of 2-methyl-5-methoxyaniline (25.3 g, 184.5 mmol), N,N-dimethylformamide (100 mL), 1-bromo-2-ethylhexane (145 g, 752 mmol), potassium carbonate (90.1 g, 652 mmol), and potassium iodide (9.3 g, 56 mmol) was stirred for 6 hours with heating and refluxing. This mixture was allowed to cool and then filtered. Water was added to the filtrate, and the resultant mixture was extracted with toluene. The organic layer obtained was concentrated and then purified by silica gel column chromatography to obtain C-10 (11.7 g; yield 18%).

<Synthesis of Intermediate C-11>

[Chem. 21]

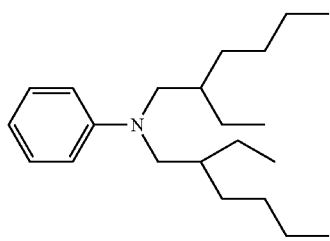

C-11

A mixture of aniline (25.0 g, 270 mmol), N,N-dimethylformamide (50 mL), 1-bromo-2-ethylhexane (156 g, 805 mmol), and potassium carbonate (148 g, 1.1 mol) was stirred at 140° C. for 18 hours. This mixture was allowed to cool and then filtered. Water was added to the filtrate, and the resultant mixture was extracted with toluene. The organic layer obtained was concentrated and then purified by silica gel column chromatography to obtain C-11 (36.2 g; yield 42%).

<Synthesis of Intermediate C-12>

[Chem. 22]

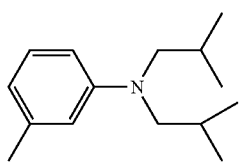

C-12

A mixture of m-toluidine (10.0 g, 93 mmol), N,N-dimethylformamide (50 mL), 1-bromo-2-methylpropane (38.4 g, 280 mmol), and potassium carbonate (51.6 g, 373 mmol) was stirred at 110° C. for 16 hours. This mixture was allowed to cool and then filtered. Water was added to the filtrate, and the resultant mixture was extracted with toluene. The organic layer obtained was concentrated and then purified by silica gel column chromatography to obtain C-12 (8.90 g; yield 43%).

Example 1

Synthesis of Dye 1

[Chem. 23]

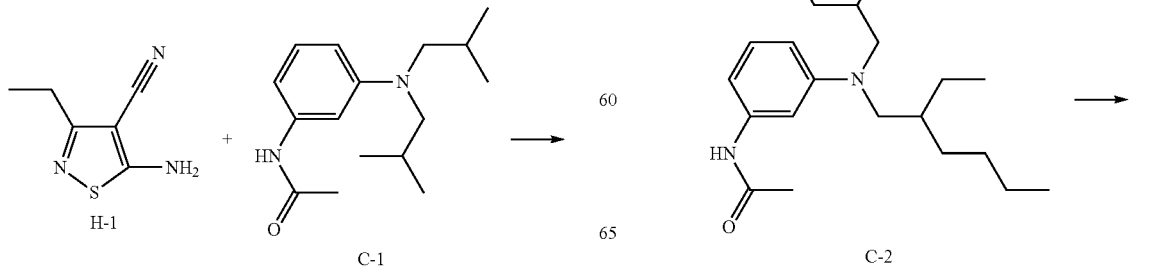

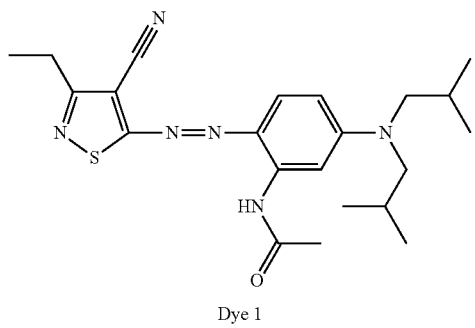

Dye 1

A mixture of H-1 (0.50 g, 3.3 mmol), glacial acetic acid (3 mL), propionic acid (0.7 mL), sulfuric acid (2.7 mL), and desalted water (0.3 mL) was cooled with an ice bath. At an internal temperature of 1° C., 44 wt % nitrosylsulfuric acid (1.0 g, 3.6 mmol) was dropped into the mixture. Thereafter, the resultant mixture was stirred for 1 hour while keeping the internal temperature at 0±5° C., thereby obtaining a diazo solution. Into another vessel were introduced C-1 (0.81 g, 3.1 mmol), tetrahydrofuran (40 mL), sulfamic acid (0.06 g, 0.6 mmol), and sodium acetate (5.7 g). The diazo solution was dropped thereinto while keeping the internal temperature at 0±5° C. by cooling with ice. In the course of the dropping, ice and tetrahydrofuran (40 mL) were added. After completion of the dropping, an aqueous sodium acetate solution was added to adjust the pH to 4. The resultant mixture was extracted with toluene, and the extract was concentrated under vacuum and purified by silica gel column chromatography to obtain dye 1 (0.45 g; yield, 32%).

Synthesis of Dye 2

[Chem. 24]

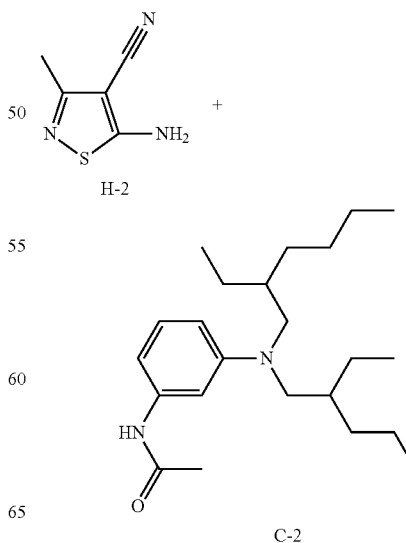

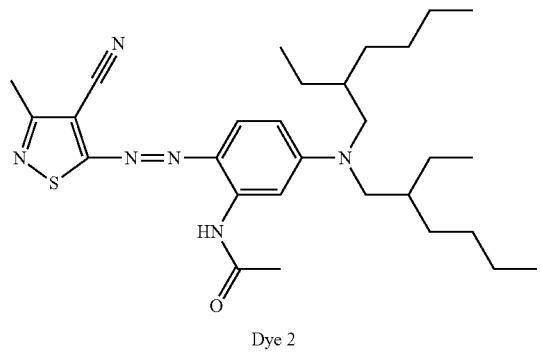

Dye 2

Dye 2 was synthesized from H-2 and C-2 in the same manner as for the synthesis of dye 1.

Synthesis of Dye 3

[Chem. 25]

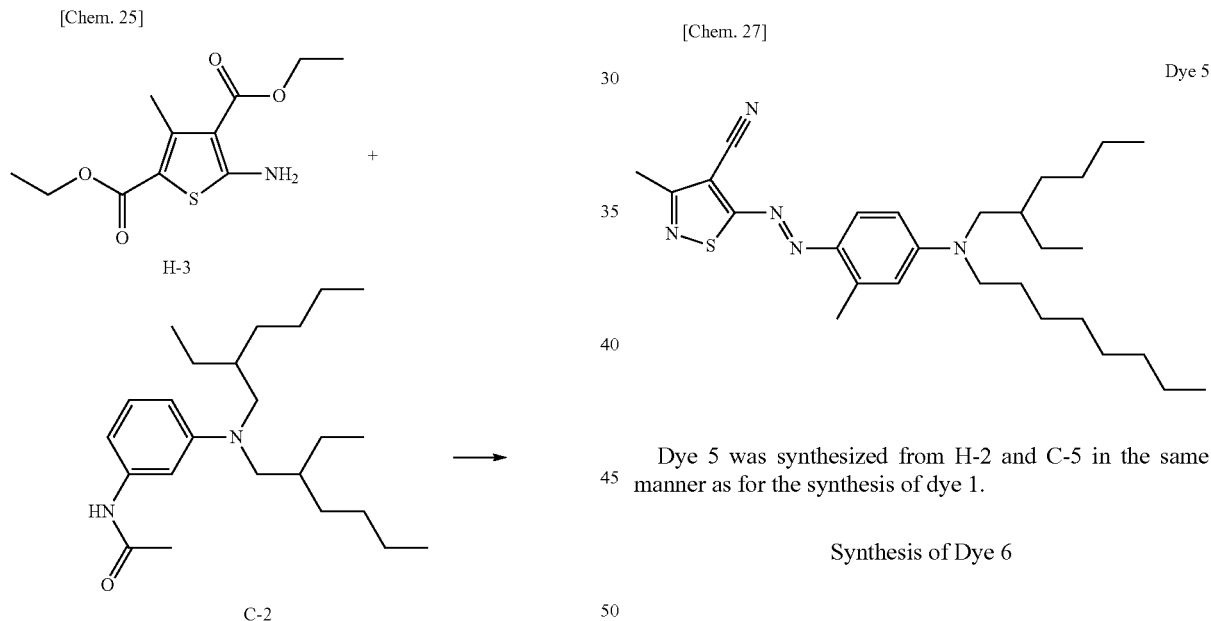

Dye 3

Dye 3 was synthesized from H-3 and C-2 in the same manner as for the synthesis of dye 1.

Synthesis of Dye 4

[Chem. 26]

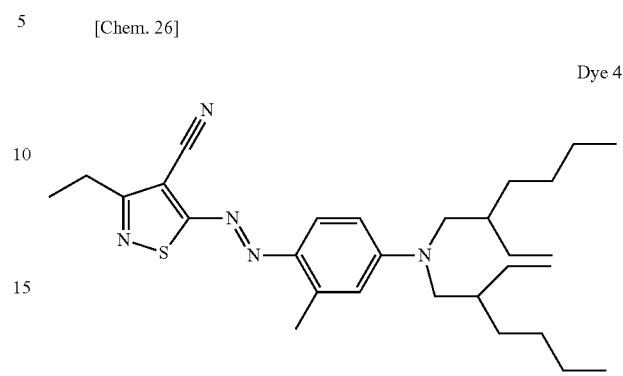

Dye 4

Dye 4 was synthesized from H-1 and C-3 in the same manner as for the synthesis of dye 1.

Synthesis of Dye 5

[Chem. 27]

Dye 5

Dye 5 was synthesized from H-2 and C-5 in the same manner as for the synthesis of dye 1.

Synthesis of Dye 6

[Chem. 28]

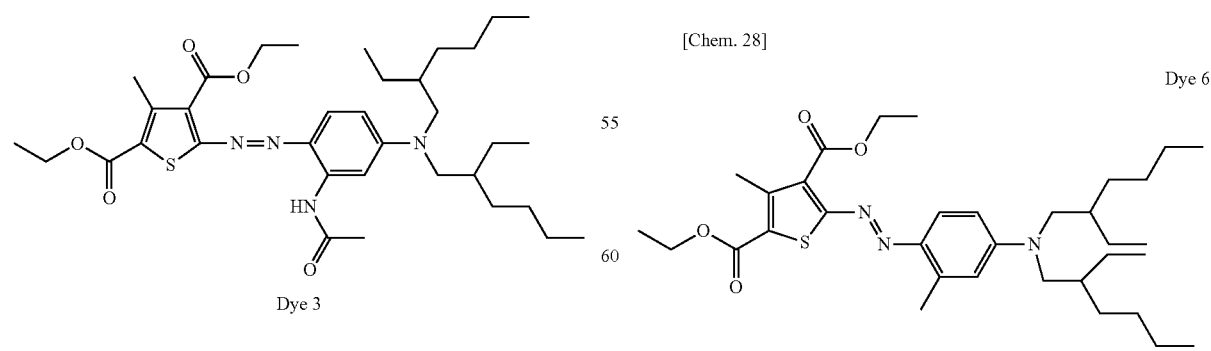

Dye 6

Dye 6 was synthesized from H-3 and C-3 in the same manner as for the synthesis of dye 1.

Synthesis of Dye 7

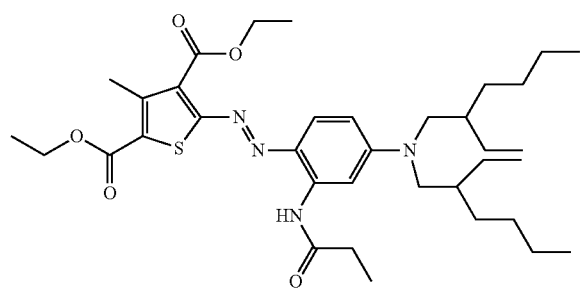

Dye 7 was synthesized from H-3 and C-6 in the same manner as for the synthesis of dye 1.

Synthesis of Dye 8

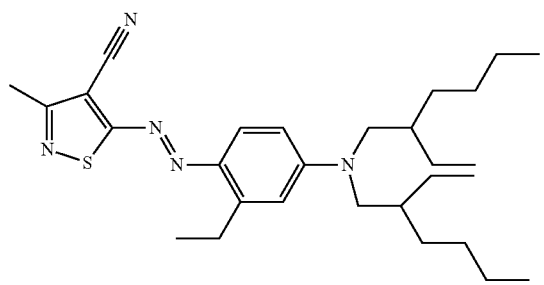

Dye 8 was synthesized from H-2 and C-7 in the same manner as for the synthesis of dye 1.

Synthesis of Dye 9

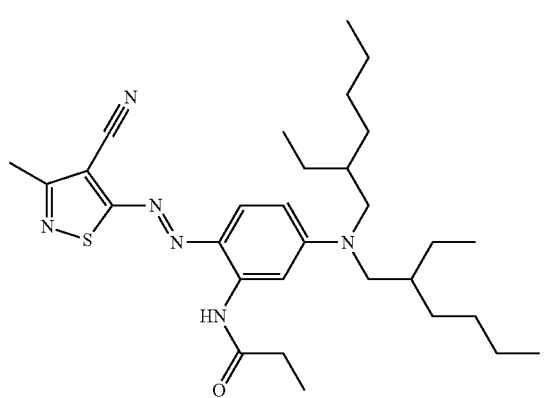

Dye 9 was synthesized from H-2 and C-6 in the same manner as for the synthesis of dye 1.

Synthesis of Dye 10

Dye 10 was synthesized from H-1 and C-2 in the same manner as for the synthesis of dye 1.

Synthesis of Dye 11

Dye 11 was synthesized from H-1 and C-8 in the same manner as for the synthesis of dye 1.

Synthesis of Dye 12

29
-continued

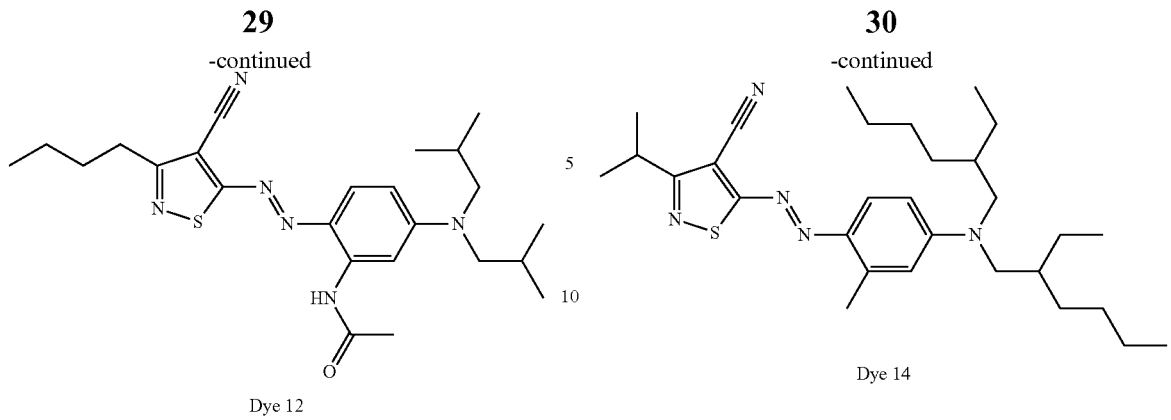

Dye 12

Dye 12 was synthesized from H-4 and C-1 in the same manner as for the synthesis of dye 1.

Synthesis of Dye 13

[Chem. 35]

Dye 13

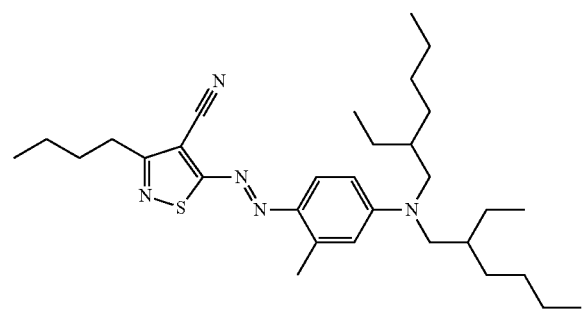

Dye 13 was synthesized from H-4 and C-3 in the same manner as for the synthesis of dye 1.

Synthesis of Dye 14

[Chem. 36]

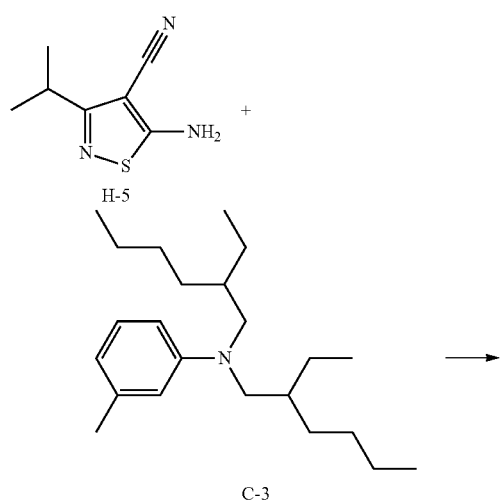

30
-continued

Dye 14

Dye 14 was synthesized from H-5 and C-3 in the same manner as for the synthesis of dye 1.

Synthesis of Dye 15

[Chem. 37]

Dye 15

Dye 15 was synthesized from H-2 and C-9 in the same manner as for the synthesis of dye 1.

Synthesis of Dye 16

[Chem. 38]

Dye 16

Dye 16 was synthesized from H-2 and C-10 in the same manner as for the synthesis of dye 1.

Synthesis of Dye 17

[Chem. 39]

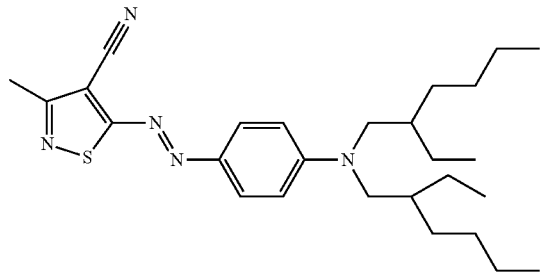

Dye 17

Dye 17 was synthesized from H-2 and C-11 in the same manner as for the synthesis of dye 1.

Synthesis of Dye 18

[Chem. 40]

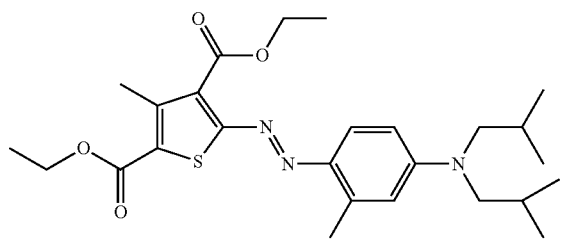

Dye 18

Dye 18 was synthesized from H-3 and C-12 in the same manner as for the synthesis of dye 1.

Synthesis of Dye 19

[Chem. 41]

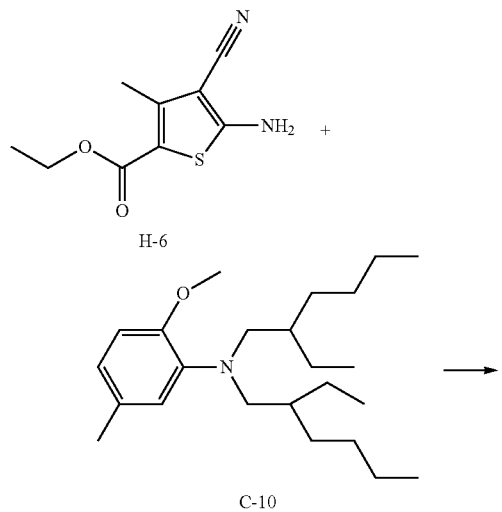

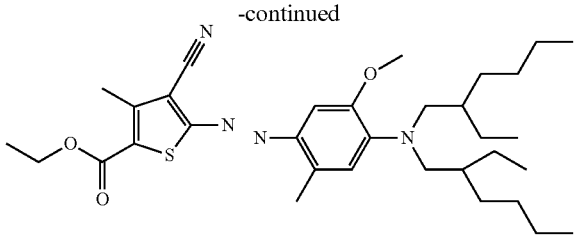

Dye 19

Dye 19 was synthesized from H-6 and C-10 in the same manner as for the synthesis of dye 1.

Synthesis of Dye 20

[Chem. 42]

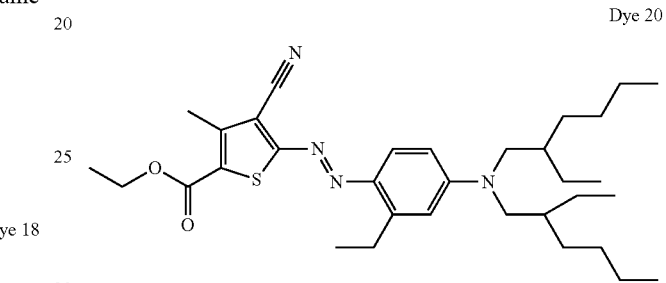

Dye 20

Dye 20 was synthesized from H-6 and C-7 in the same manner as for the synthesis of dye 1.

<Comparative Dye 1>

The compound No. 28 described in JP-A-02-241784 was synthesized as comparative dye 1.

[Chem. 43]

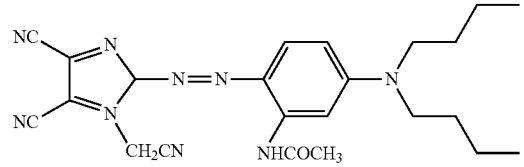

Comparative Dye 1

<Comparative Dye 2>

Comparative dye 2 was synthesized in accordance with the Example 1 of International Publication WO 2010/031860 and JP-A-11-124510.

[Chem. 44]

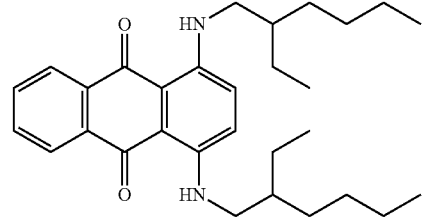

Comparative Dye 2

<Comparative Dye 3>

The compound M-2 in JP-A-01-136787 was synthesized as comparative dye 3.

[Chem. 45]

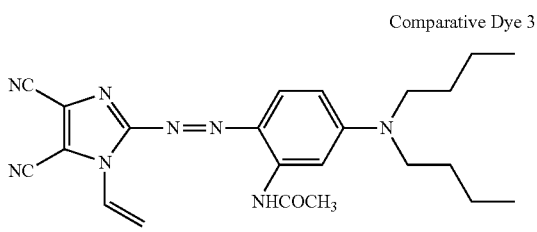

Comparative Dye 3

<Test Results>

Dyes 1 to 20 and comparative dyes 1 to 3 were subjected to a solubility test for examining solubility in n-decane, tetradecane, Isopar M, Isopar and decalin and to a light fastness test.

The solution color, absorption-maximum wavelength (λmax), solubility, and εC for n-decane are summarized in Table 3. Similarly, the test results obtained with tetradecane are summarized in Table 4, the test results obtained with Isopar M are summarized in Table 5, the test results obtained with Isopar G are summarized in Table 6, and the test results obtained with decalin are summarized in Table 7. Furthermore, the results of the test for examining light fastness in each solvent are summarized in Table 8.

<Solubility Test>

The solubility of each dye in n-decane, tetradecane, Isopar M, Isopar G, and decalin was examined in the following manner. Each dye was added to each solvent until a dissolution residue came to remain, and this mixture was subjected to a 30-minute ultrasonic treatment at 30 degrees. The resultant mixture was allowed to stand at 5° C. for 24 hours and then subjected to centrifugal filtration (centrifugal force, 5,200×g) with a 0.1-μm filter using a microcentrifuge. The saturated solution obtained was diluted to an adequate concentration, and the solubility of each dye was calculated from a relationship with an extinction coefficient determined beforehand. Furthermore, the value of the product of the molar extinction coefficient ε ($Lmol^{-1}cm^{-1}$) and the concentration C ($molL^{-1}$) of the saturated solution, εC, was determined.

<Light Fastness Test>

The light fastness of each dye was examined in the following manner. One milligram of each dye was dissolved in 250 mL of each of n-decane, tetradecane, Isopar M, and Isopar G, and the solution was irradiated with light for 2 hours using photoreaction apparatus UVL-400HA (400-W high-pressure mercury lamp), manufactured by Riko-Kagaku Sangyo Co., Ltd. During the irradiation, the vessel was cooled with a coolant to keep the internal temperature at 10-30° C. The retention of the dye was determined through the following calculation to evaluate the light fastness.

Retention of dye=(absorbance at absorption-maximum wavelength after irradiation)/(absorbance at absorption-maximum wavelength before irradiation)

TABLE 3

Results of n-decane solubility test

| Dye | Color tone | λmax | Solubility | εC ($cm^{-1}$) |
|---|---|---|---|---|
| Dye 1 | red | 538 nm | 1.1% | 1000 |
| Dye 2 | red | 543 nm | 7.9% | 6600 |
| Dye 3 | red | 537 nm | 2.4% | 1300 |
| Dye 4 | red | 527 nm | 6.6% | 5700 |
| Dye 5 | red | 523 nm | 2.1% | 1300 |

TABLE 3-continued

Results of n-decane solubility test

| Dye | Color tone | λmax | Solubility | εC ($cm^{-1}$) |
|---|---|---|---|---|
| Dye 6 | red | 504 nm | 8.4% | 3200 |
| Dye 7 | red | 536 nm | 10.3% | 5700 |
| Dye 8 | red | 533 nm | 10% | 6500 |
| Dye 9 | red | 543 nm | 13% | 11000 |
| Dye 10 | red | 543 nm | 20% | 17000 |
| Dye 11 | red | 535 nm | 4.2% | 4300 |
| Dye 12 | red | 543 nm | 5.7% | 4100 |
| Dye 13 | red | 527 nm | 5.9% | 3700 |
| Dye 14 | red | 527 nm | 4.8% | 2800 |
| Dye 15 | red | 535 nm | 9.7% | 8300 |
| Dye 16 | red | 563 nm | 3.7% | 2300 |
| Dye 17 | red | 523 nm | 9.2% | 12000 |
| Dye 18 | red | 498 nm | 1.7% | 1000 |
| Dye 19 | red | 579 nm | 8.2% | 7900 |
| Dye 20 | red | 546 nm | 9.7% | 6000 |
| Comparative dye 1 | red | 525 nm | ≤0.01% | ≤10 |
| Comparative dye 2 | blue | 652 nm | 6.6% | 2000 |
| Comparative dye 3 | colorless | unable to be measured | ≤0.01% | ≤10 |

TABLE 4

Results of tetradecane solubility test

| Dye | Color tone | λmax | Solubility | εC ($cm^{-1}$) |
|---|---|---|---|---|
| Dye 2 | red | 545 nm | 5.4% | 4900 |
| Dye 4 | red | 530 nm | 6.8% | 5200 |
| Dye 7 | red | 538 nm | 9.7% | 5400 |
| Dye 8 | red | 534 nm | 3.9% | 2800 |
| Dye 9 | red | 544 nm | 8.5% | 7400 |
| Dye 10 | red | 544 nm | 19% | 16700 |
| Comparative dye 2 | blue | 651 nm | 5.7% | 1600 |
| Comparative dye 3 | colorless | unable to be measured | ≤0.01% | ≤10 |

TABLE 5

Results of Isopar M solubility test

| Dye | Color tone | λmax | Solubility | εC ($cm^{-1}$) |
|---|---|---|---|---|
| Dye 2 | red | 544 nm | 4.32% | 4000 |
| Dye 4 | red | 530 nm | 8.51% | 6000 |
| Dye 7 | red | 536 nm | 10% | 6300 |
| Dye 8 | red | 534 nm | 3.4% | 2500 |
| Dye 9 | red | 544 nm | 9.8% | 8900 |
| Dye 10 | red | 542 nm | 20% | 18600 |
| Comparative dye 2 | blue | 650 nm | 3.6% | 1000 |
| Comparative dye 3 | colorless | unable to be measured | ≤0.01% | ≤10 |

TABLE 6

Results of Isopar G solubility test

| Dye | Color tone | λmax | Solubility | εC ($cm^{-1}$) |
|---|---|---|---|---|
| Dye 2 | red | 542 nm | 5.7% | 5000 |
| Dye 4 | red | 526 nm | 7.4% | 4900 |
| Dye 7 | red | 535 nm | 10% | 6000 |
| Dye 8 | red | 533 nm | 5.17% | 3600 |
| Dye 9 | red | 543 nm | 13.3% | 11500 |
| Dye 10 | red | 542 nm | 20% | 18600 |

TABLE 6-continued

Results of Isopar G solubility test

| Dye | Color tone | λmax | Solubility | εC (cm⁻¹) |
|---|---|---|---|---|
| Comparative dye 2 | blue | 649 nm | 4.3% | 1200 |
| Comparative dye 3 | colorless | unable to be measured | ≤0.01% | ≤10 |

TABLE 7

Results of decalin solubility test

| Dye | Color tone | λmax | Solubility | εC (cm⁻¹) |
|---|---|---|---|---|
| Dye 2 | red | 547 nm | 24.5% | 24000 |
| Dye 4 | red | 534 nm | 6.5% | 5200 |
| Dye 9 | red | 547 nm | 9.1% | 8500 |
| Dye 10 | red | 546 nm | 6.7% | 6600 |
| Comparative dye 2 | blue | 645 nm | 9.98% | 3400 |
| Comparative dye 3 | red | 520 nm | ≤0.01% | ≤10 |

TABLE 8

Results of light fastness test

| Dye | Solvent | | | |
|---|---|---|---|---|
| | n-decane | tetradecane | Isopar M | Isopar G |
| Dye 1 | 97% | | | |
| Dye 2 | 97% | 94% | 100% | 100% |
| Dye 3 | 92% | | | |
| Dye 4 | 96% | 82% | 95% | 98% |
| Dye 7 | 98% | 81% | 87% | 98% |
| Dye 10 | 99% | | | |
| Comparative dye 1 | 45% | | | |
| Comparative dye 2 | 92% | 99% | 90% | 85% |
| Comparative dye 3 | 76% | | | |

It was found from the test results that dyes 1 to 20, when dissolved in each of the low-polarity solvents, show an exceedingly high solubility and a large value of εC and have satisfactory light fastness, as compared with comparative dyes 1 and 3, which have the same color tone. Comparative dye 2, which is an anthraquinone dye, had a large value of λmax and a small value of εC.

Example 2

Preparation of Ink 1

Dye composition 1, which was composed of dye 4 and the following yellow dye 2, blue dye 1, and blue dye 2 and which had the recipe shown below, was dissolved in 1.28 g of n-decane (manufactured by Tokyo Kasei Kogyo Co., Ltd.) to prepare ink 1, which was black. The recipe was as shown in Table 9.

Preparation of Ink 2

Dye composition 2, which was composed of dye 2 and the following yellow dye 1 and blue dye 2 and which had the recipe shown below, was dissolved in 30.0 g of n-decane (manufactured by Tokyo Kasei Kogyo Co., Ltd.) to prepare ink 2, which was black. The recipe was as shown in Table 9.

<Yellow Dye 1>
The following compound was synthesized in accordance with the Example 1 of International Publication WO 2009/063880.

[Chem. 46]

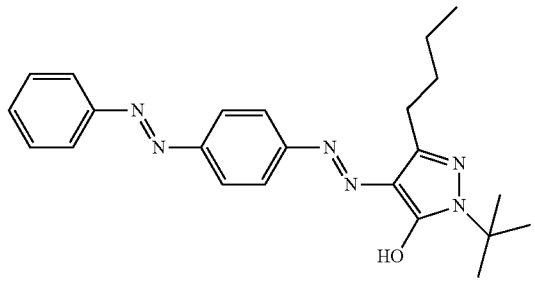

<Yellow Dye 2>
The following compound was synthesized in accordance with the Example 2 of International Publication WO 2009/063880.

[Chem. 47]

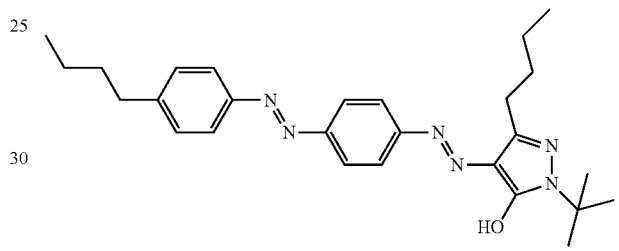

<Blue Dye 1>
The following compound was synthesized in accordance with the Example 1 of International Publication WO 2010/031860.

[Chem. 48]

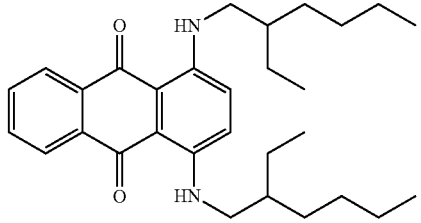

<Blue Dye 2>
The following compound was synthesized in accordance with the Example 3 of JP-A-2000-313174.

[Chem. 49]

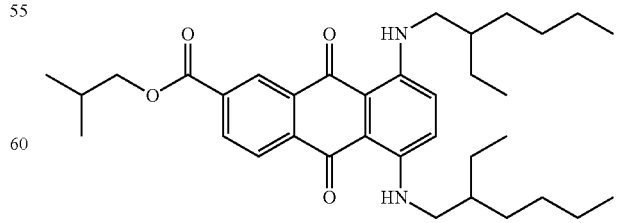

<Comparative Ink>
Sudan Black B (manufactured by Tokyo Kasei Kogyo Co., Ltd.), which is a commercial oil-soluble black dye, was added to n-decane until a dissolution residue came to remain, and this mixture was subjected to a 30-minute ultrasonic treatment at 30 degrees. The resultant mixture was allowed to stand at 5° C. for 24 hours and then subjected to centrifugal filtration (centrifugal force, 5,200×g) with a 0.1-μm filter using a microcentrifuge. The saturated n-decane solution obtained was diluted to an adequate concentration, and the solubility of the dye was calculated from a relationship with an extinction coefficient determined beforehand. As a result, the solubility thereof was found to be 0.13%.

A saturated decane solution of the Sudan Black B was prepared as a comparative ink.

Sudan Black B

[Chem. 50]

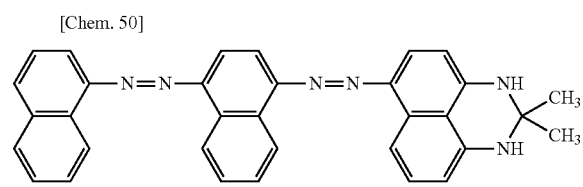

TABLE 9

|  | Solvent | Red dye | Yellow dye | Blue dye |  | Black dye |
|---|---|---|---|---|---|---|
| Ink 1 | n-decane 1.28 g | dye 4 153 mg | yellow dye 2 93 mg | blue dye 1 122 mg | blue dye 2 360 mg | — |
| Ink 2 | n-decane 30.0 g | dye 2 1.21 g | yellow dye 1 1.93 g | blue dye 2 7.20 g |  | — |
| Comparative ink | n-decane 10.0 g | — | — | — |  | Sudan Black B 13.0 mg |

<Hue Evaluation>

Black inks 1 and 2 and the comparative ink were examined for spectrum using a cell having an optical path length of 0.01 mm, and a color measurement was made using the color calculation program belonging to Hitachi spectrophotometer U-4100, under the conditions of illuminant D65 and a viewing angle of 2 degrees. Thus, each ink was quantitatively evaluated for hue. Incidentally, in the CIE color space chromaticity coordinates L*a*b*, L* represents lightness; L*=0 and L*=100 indicate black and white, respectively, in terms of the color of diffused light. Consequently, the closer to 0 the value of L*, the more the color is preferred as black.

The results of the color calculation for each of inks 1 and 2 and the comparative ink are shown in Table 10.

TABLE 10

|  |  | Results of color calculation | | |
|---|---|---|---|---|
|  | Solvent | L* | a* | b* |
| Ink 1 | n-decane | 0.088 | 0.40 | 0.092 |
| Ink 2 | n-decane | 1.18 | 2.58 | 1.36 |
| Comparative ink | n-decane | 95.2 | 1.13 | −1.04 |

It can be seen from Table 10 that inks 1 and 2 have a value of L* close to 0, as compared with the comparative ink, and are satisfactory black inks with an excellent black hue.

Example 3

Preparation of Red Inks

Dyes were dissolved in solvents in accordance with the recipes shown in Table 11 to prepare inks 3 to 9, which were red. In each recipe, the dye was completely dissolved in the solvent.

TABLE 11

|  | Dye | Solvent | Amount of solvent | Amount of dye | Concentration |
|---|---|---|---|---|---|
| Ink 3 | dye 2 | tetradecane | 19.6 g | 0.40 g | 2% |
| Ink 4 | dye 2 | xylene | 19.6 g | 0.40 g | 2% |
| Ink 5 | dye 4 | Isopar M | 19.9 g | 0.40 g | 2% |
| Ink 6 | dye 8 | Isopar G | 19.6 g | 0.40 g | 2% |
| Ink 7 | dye 9 | decalin | 19.7 g | 0.40 g | 2% |
| Ink 8 | dye 10 | n-decane | 19.6 g | 0.40 g | 2% |
| Ink 9 | dye 10 | n-decane | 18.1 g | 1.00 g | 5% |

<Viscosity Measurement>

The viscosity of each of inks 3 to 9 and of the solvents of these inks was measured using viscometer VISCOMATE MODEL VM-10A, manufactured by CAC MATERIALS CO., Ltd. The measurement was made while regulating the temperature of each solvent or ink so as to be as close as possible to 25° C. The temperatures given in Table 12 are the actual liquid temperatures during the measurement.

TABLE 12

|  | Solvent | | Ink | |
|---|---|---|---|---|
|  | Viscosity/ $m^2 s^{-1}$ | Temperature/ ° C. | Viscosity/ $m^2 s^{-1}$ | Temperature/ ° C. |
| Ink 3 | 2.90 | 27.4 | 1.87 | 24.5 |
| Ink 4 | 1.03 | 27.6 | 0.74 | 26.1 |
| Ink 5 | 2.05 | 27.5 | 2.97 | 25.9 |
| Ink 6 | 0.87 | 27.5 | 1.04 | 26.4 |
| Ink 7 | 2.97 | 27.4 | 2.57 | 26.7 |
| Ink 8 | 1.11 | 28.1 | 0.87 | 27.4 |
| Ink 9 | 1.11 | 28.1 | 1.02 | 27.3 |

<Determination of Relative Permittivity>

The relative permittivity of each of inks 3 to 9 and the solvents of these inks was determined at room temperature (25° C.) by the impedance meter method using precision LCR meter 4284A, manufactured by Agilent Technologies, Inc. Each ink or solvent was sandwiched between flat glass substrates which each had an ITO electrode and which had been disposed parallel so as to face each other at an electrode spacing of 30 μm. Thereafter, the equivalent parallel capacity was measured while applying a test signal voltage of 0.1 V at a measuring frequency of 1 kHz. The relative permittivity was determined through the calculation according to the following equation to evaluate the ink.

Relative permittivity=(equivalent parallel capacity)×(electrode spacing)/(electrode area)/(permittivity in vacuum ($\epsilon_0$))

TABLE 13

| | Permittivity at 1 kHz | |
|---|---|---|
| | Solvent | Ink |
| Ink 3 | 2.20 | 1.87 |
| Ink 4 | 1.97 | 2.57 |
| Ink 5 | 2.02 | 2.23 |
| Ink 6 | 2.40 | 2.18 |
| Ink 7 | 2.06 | 2.23 |
| Ink 8 | 2.03 | 2.06 |
| Ink 9 | 2.03 | 2.24 |

While the invention has been described in detail and with reference to specific embodiments thereof, it will be apparent to one skilled in the art that various changes and modifications can be made therein without departing from the spirit and scope thereof. This application is based on a Japanese patent application filed on Sep. 10, 2010 (Application No. 2010-203335), a Japanese patent application filed on Jan. 7, 2011 (Application No. 2011-002372), and a Japanese patent application filed on Apr. 28, 2011 (Application No. 2011-102267), the contents thereof being incorporated herein by reference.

INDUSTRIAL APPLICABILITY

The ink and heterocyclic azo dye of the invention are especially suitable for use in electrowetting displays such as, for example, electronic paper.

The invention claimed is:

1. An ink which comprises: a low-polarity solvent having a relative permittivity, as measured at a frequency of 1 kHz, of 3 or less; and a heterocyclic azo dye, wherein the heterocyclic azo dye is a dye represented by the following general formula (I):

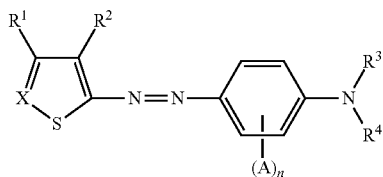

(I)

wherein
$R^1$ represents a hydrogen atom or an optionally substituted alkyl group having 1-20 carbon atoms,
$R^2$ represents a cyano group or a $COOR^5$ group,
$R^5$ represents an optionally substituted alkyl group having 1-20 carbon atoms,
$R^3$ and $R^4$ each independently represent an optionally substituted alkyl group having 5-20 carbon atoms,
A represents a hydrogen atom, a halogen atom, an optionally substituted alkyl group having 1-20 carbon atoms, an optionally substituted alkoxy group having 1-20 carbon atoms, or an $NHCOR^6$ group,
n represents an integer of 1-4, and when n is 2 or larger, the A's may be the same or different,
$R^6$ represents a hydrogen atom, an alkyl group having 1-20 carbon atoms, an alkoxy group having 1-20 carbon atoms, or an aryl group,
X represents a nitrogen atom or a methine group optionally substituted with a substituent selected from the group consisting of an optionally substituted alkyl group having 1-10 carbon atoms, a $COOR^7$ group, and cyano, wherein $R^7$ represents an optionally substituted alkyl group having 1-20 carbon atoms, and
$R^3$ and $R^4$ may be bonded to each other to form a cyclic structure.

2. The ink according to claim 1, wherein the low-polarity solvent comprises at least one member selected from the group consisting of hydrocarbon solvents, silicone oils, and fluorocarbon solvents.

3. The ink according to claim 1, wherein the heterocyclic azo dye is a dye in which, when dissolving the dye in n-decane, an absorption-maximum wavelength in the wavelength range of 350-750 nm is in the range of 450-600 nm, and the product of a molar extinction coefficient $\epsilon$ ($Lmol^{-1}cm^{-1}$) at the absorption-maximum wavelength and a concentration C ($molL^{-1}$) of saturated solution in the solvent at room temperature (25° C.), $\epsilon C$, has a value of 500 $cm^{-1}$ or larger.

4. The ink according to claim 1, which further comprises at least one of a pyrazole dye and an alkylamine-substituted anthraquinone dye.

5. The ink according to claim 4, wherein the pyrazole dye is represented by the following general formula (II) and the alkylamine-substituted anthraquinone dye is represented by the following general formula (III):

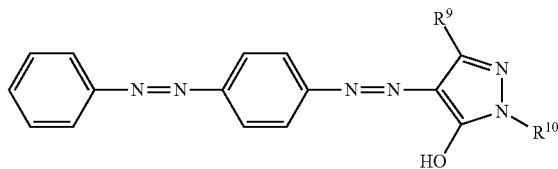

(II)

wherein $R^9$ represents an alkyl group having 2-10 carbon atoms, and $R^{10}$ represents an alkyl group having 3-10 carbon atoms, and the phenyl group and the phenylene group each may independently have a substituent;

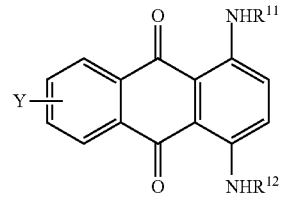

(III)

wherein Y represents a hydrogen atom or a $COOR^{13}$ group, and $R^{11}$ to $R^{13}$ each independently represent an optionally substituted alkyl group having 1-20 carbon atoms, at least one of $R^{11}$ to $R^{13}$ is an optionally substituted branched alkyl group having 4-20 carbon atoms, and the anthraquinone ring may have any substituent other than the Y, $NHR^{11}$ and $NHR^{12}$.

6. A display or optical shutter comprising the ink according to claim 1.

7. A display which comprises a display part containing the ink according to claim 1, in which an image is displayed by controlling voltage application to the display part.

8. The display according to claim 7, wherein the display part contains electrophoretic particles or an aqueous medium.

9. The display according to claim 7, wherein an image is displayed by changing the coloration by means of voltage application.

10. The display according to claim 7, wherein an image is displayed by an electrowetting system or an electrophoretic system.

11. An electronic paper which comprises the display according to claim 7.

12. A heterocyclic azo dye represented by the following general formula (IV):

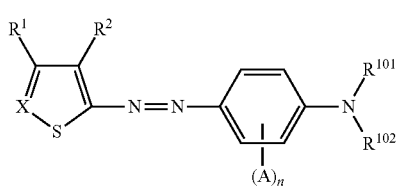

(IV)

wherein
$R^1$ represents a hydrogen atom or an optionally substituted alkyl group having 1-20 carbon atoms,
$R^2$ represents a cyano group or a $COOR^5$ group,
$R^5$ represents an optionally substituted alkyl group having 1-20 carbon atoms,
$R^{101}$ and $R^{102}$ each independently represent an optionally substituted alkyl group having 5-20 carbon atoms,
A represents a hydrogen atom, a halogen atom, an optionally substituted alkyl group having 1-20 carbon atoms, an optionally substituted alkoxy group having 1-20 carbon atoms, or an $NHCOR^6$ group,
n represents an integer of 1-4, and when n is 2 or larger, the A's may be the same or different,
$R^6$ represents a hydrogen atom, an alkyl group having 1-20 carbon atoms, an alkoxy group having 1-20 carbon atoms, or an aryl group,
X represents a nitrogen atom or a methine group optionally substituted with a substituent selected from the group consisting of an optionally substituted alkyl group having 1-10 carbon atoms, a $COOR^7$ group, and cyano, wherein $R^7$ represents an optionally substituted alkyl group having 1-20 carbon atoms, and
$R^{101}$ and $R^{102}$ may be bonded to each other to form a cyclic structure.

13. The ink according to claim 1, wherein X represents a nitrogen atom.

14. The ink according to claim 1, wherein X represents an optionally substituted methine group.

15. The ink according to claim 1, wherein $R^2$ represents a cyano group.

16. The ink according to claim 1, wherein $R^2$ represents a $COOR^5$ group.

17. The ink according to claim 1, wherein at least one A represents a halogen atom, an optionally substituted alkyl group having 1-20 carbon atoms, an optionally substituted alkoxy group having 1-20 carbon atoms, or an $NHCOR^6$ group.

18. An ink which comprises: a low-polarity solvent having a relative permittivity, as measured at a frequency of 1 kHz, of 3 or less; and a heterocyclic azo dye, wherein the heterocyclic azo dye is a dye represented by the following general formula (I):

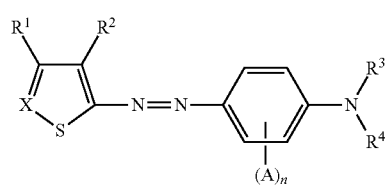

(I)

wherein
$R^1$ represents a hydrogen atom or an optionally substituted alkyl group having 1-20 carbon atoms,
$R^2$ represents a cyano group or a $COOR^5$ group,
$R^5$ represents an optionally substituted alkyl group having 1-20 carbon atoms,
$R^3$ and $R^4$ each independently represent an optionally substituted alkyl group having 4-20 carbon atoms in which at least one of $R^3$ and $R^4$ is branched,
A represents a hydrogen atom, a halogen atom, an optionally substituted alkyl group having 1-20 carbon atoms, an optionally substituted alkoxy group having 1-20 carbon atoms, or an $NHCOR^6$ group,
n represents an integer of 1-4, and when n is 2 or larger, the A's may be the same or different,
$R^6$ represents a hydrogen atom, an alkyl group having 1-20 carbon atoms, an alkoxy group having 1-20 carbon atoms, or an aryl group,
X represents a nitrogen atom or a methine group optionally substituted with a substituent selected from the group consisting of an optionally substituted alkyl group having 1-10 carbon atoms, a $COOR^7$ group, and cyano, wherein $R^7$ represents an optionally substituted alkyl group having 1-20 carbon atoms, and
$R^3$ and $R^4$ may be bonded to each other to form a cyclic structure.

* * * * *